(12) United States Patent
Alfarra

(10) Patent No.: US 10,682,018 B2
(45) Date of Patent: Jun. 16, 2020

(54) AUTOMATED FOOD PREPARATION AND DISPENSING

(71) Applicant: Anas Alfarra, Bellevue, WA (US)

(72) Inventor: Anas Alfarra, Bellevue, WA (US)

(*) Notice: Subject to any disclaimer, the term of this patent is extended or adjusted under 35 U.S.C. 154(b) by 186 days.

(21) Appl. No.: 16/120,227

(22) Filed: Sep. 1, 2018

(65) Prior Publication Data

US 2019/0069728 A1 Mar. 7, 2019

Related U.S. Application Data

(60) Provisional application No. 62/553,819, filed on Sep. 2, 2017.

(51) Int. Cl.

| | |
|---|---|
| *A23L 5/20* | (2016.01) |
| *A47J 44/00* | (2006.01) |
| *G06Q 50/12* | (2012.01) |
| *G06Q 10/08* | (2012.01) |
| *A23L 5/30* | (2016.01) |
| *H04N 7/18* | (2006.01) |

(Continued)

(52) U.S. Cl.
CPC ............. *A47J 44/00* (2013.01); *A22B 5/007* (2013.01); *A22B 5/0041* (2013.01); *A22C 17/002* (2013.01); *A22C 17/0086* (2013.01); *A23B 7/01* (2013.01); *A23L 3/01* (2013.01); *A23L 5/15* (2016.08); *A23L 5/20* (2016.08); *A23L 5/30* (2016.08); *A23L 5/34* (2016.08); *A23L 5/36* (2016.08); *A23L 11/30* (2016.08); *A23L 33/30* (2016.08); *A23N 12/02* (2013.01); *A23N 15/02* (2013.01); *A23N 15/06* (2013.01); *A47J 17/14* (2013.01); *A47J 43/24* (2013.01); *G06Q 10/083* (2013.01); *G06Q 10/087* (2013.01); *G06Q 50/12* (2013.01); *H04N 7/181* (2013.01); *B26D 2210/02* (2013.01); *G06F 3/04817* (2013.01)

(58) Field of Classification Search
CPC . A47J 44/00; A47J 17/00–17/20; A47J 43/24; A23L 33/30; A23L 5/30; A23L 3/01; A23L 5/34; A23L 5/15; A23L 5/20; A23L 5/36; A23L 11/30; A23B 7/01; G06Q 50/12; G06Q 10/087; G06Q 10/083; H04N 7/181; G06F 3/04817; A23N 12/02–12/023; A23N 15/00–15/12; B26D 2210/02–2210/08; A22B 5/0017–5/007; A22C 17/0073–17/0086
USPC ........... 426/231, 478–485, 518; 99/537–643; 452/150–157; 83/34–36, 358–372, 923, 83/932
See application file for complete search history.

(56) References Cited

U.S. PATENT DOCUMENTS

| | | | | |
|---|---|---|---|---|
| 4,226,540 A | * | 10/1980 | Barten | ............... G01N 33/12 356/445 |
| 4,581,632 A | * | 4/1986 | Davis | ............... G01N 21/88 250/223 R |

(Continued)

*Primary Examiner* — Drew E Becker

(57) ABSTRACT

The disclosed technology includes a food system that prepares food based on a user's preferences and environment (e.g., health and diet, tastes, availability of food, costs, location, and what is stored or available for the food preparation system). The food system can store, cool, serve, prepare, juice, recognize with an antenna array, cut, weigh, sanitize, or compost food. The food system can include a robotic arm or water jet for cutting a food item. The disclosed technology improves food consumption for users based on diet and observed behavior (e.g., tracking caloric intake and exercise).

20 Claims, 16 Drawing Sheets

(51) Int. Cl.
  *A23L 5/10* (2016.01)
  *A23L 33/00* (2016.01)
  *A23B 7/01* (2006.01)
  *A23L 3/01* (2006.01)
  *A22C 17/00* (2006.01)
  *A23L 11/30* (2016.01)
  *A47J 17/14* (2006.01)
  *A47J 43/24* (2006.01)
  *A23N 15/06* (2006.01)
  *A22B 5/00* (2006.01)
  *A23N 15/02* (2006.01)
  *A23N 12/02* (2006.01)
  *G06F 3/0481* (2013.01)

(56) References Cited

U.S. PATENT DOCUMENTS

| | | | | |
|---|---|---|---|---|
| 4,831,922 A | * | 5/1989 | Cogan | A23N 7/02 250/559.21 |
| 4,847,954 A | * | 7/1989 | Lapeyre | A22C 25/00 452/158 |
| 5,133,687 A | * | 7/1992 | Malloy | A22B 5/0029 452/149 |
| 5,415,083 A | * | 5/1995 | Nagaoka | A23N 15/02 99/491 |
| 6,132,784 A | * | 10/2000 | Brandt | A23B 7/015 422/186.3 |
| 6,198,834 B1 | * | 3/2001 | Belk | A22B 5/007 348/89 |
| 6,204,763 B1 | | 3/2001 | Sone | |
| 6,623,348 B1 | * | 9/2003 | O'Neill | A22B 5/0029 452/133 |
| 7,007,595 B2 | * | 3/2006 | Ozery | B26D 5/34 83/77 |
| 7,196,625 B1 | | 3/2007 | Nguyen | |
| 7,281,468 B2 | * | 10/2007 | Frem | G07F 9/105 99/334 |
| 7,841,264 B2 | * | 11/2010 | Kim | B26D 3/10 83/13 |
| 9,091,673 B2 | * | 7/2015 | Fern | A22B 5/0041 |
| 2003/0056627 A1 | * | 3/2003 | Hubert | A23N 15/003 83/13 |
| 2006/0156878 A1 | * | 7/2006 | Faires | B65G 47/31 83/13 |
| 2008/0086374 A1 | | 4/2008 | Aitken et al. | |
| 2008/0289515 A1 | * | 11/2008 | Knorr | A23N 15/02 99/640 |
| 2009/0274811 A1 | * | 11/2009 | Lundberg | A23L 19/09 426/453 |
| 2009/0282859 A1 | | 11/2009 | Glielmo et al. | |
| 2011/0293797 A1 | * | 12/2011 | Pryor | G05B 19/4183 426/231 |
| 2016/0162715 A1 | | 6/2016 | Luk et al. | |
| 2017/0151686 A1 | * | 6/2017 | Sunter | A22C 17/0086 |

* cited by examiner

AUTOMATED FOOD PREPARATION AND DISPENSING

CROSS-REFERENCE TO RELATED APPLICATION

This application claims benefit to U.S. Provisional Patent Application No. 62/553,819, filed Sep. 2, 2017, and titled "Automated Food Preparation and Dispensing," which is identified in the Application Data Sheet of the present application and hereby incorporated by reference in its entirety under 37 CFR 1.57.

BACKGROUND

Humans struggle to maintain a healthy diet for several reasons, and an unhealthy diet can lead to an unsatisfactory lifestyle or medical conditions. Some reasons for this struggle are food perishability, high labor cost associated with preparing food, lack of portable temperature-controlled storage, dietary habits, lifestyles, accessibility to healthy food, and difficulty to prepare food quickly and locally.

To mitigate an unhealthy diet, many consumers and even restaurants use computerized inventory systems for storing fresh and healthy food such as fruit or vegetables for a salad. Computerized inventory systems include sensors for detecting the presence of inventory items, and an inventory processor for restocking of those items when inventory levels fall below a threshold. The computerized inventory systems help people eat healthy food because they increase the availability of fresh food and reduce resources required to maintain the inventory.

However, even with these computerized inventory systems, it is difficult to eat healthy because healthy food perishes quickly. For example, ingredients for a healthy organic salad may only last a few days or less inside of a refrigerator, and parts of the ingredients (e.g., avocados) can perish before other ingredients (e.g., lettuce). Thus, a consumer or business owner needs to frequently monitor the health of perishable goods. Even more, a consumer or business owner may need to remove some ingredients and leave others (e.g., remove avocados and keep the lettuce), which requires time and resources.

Accordingly, a need exists for technology that overcomes these problems and provides additional benefits.

DETAILED DESCRIPTION

Figure 1:
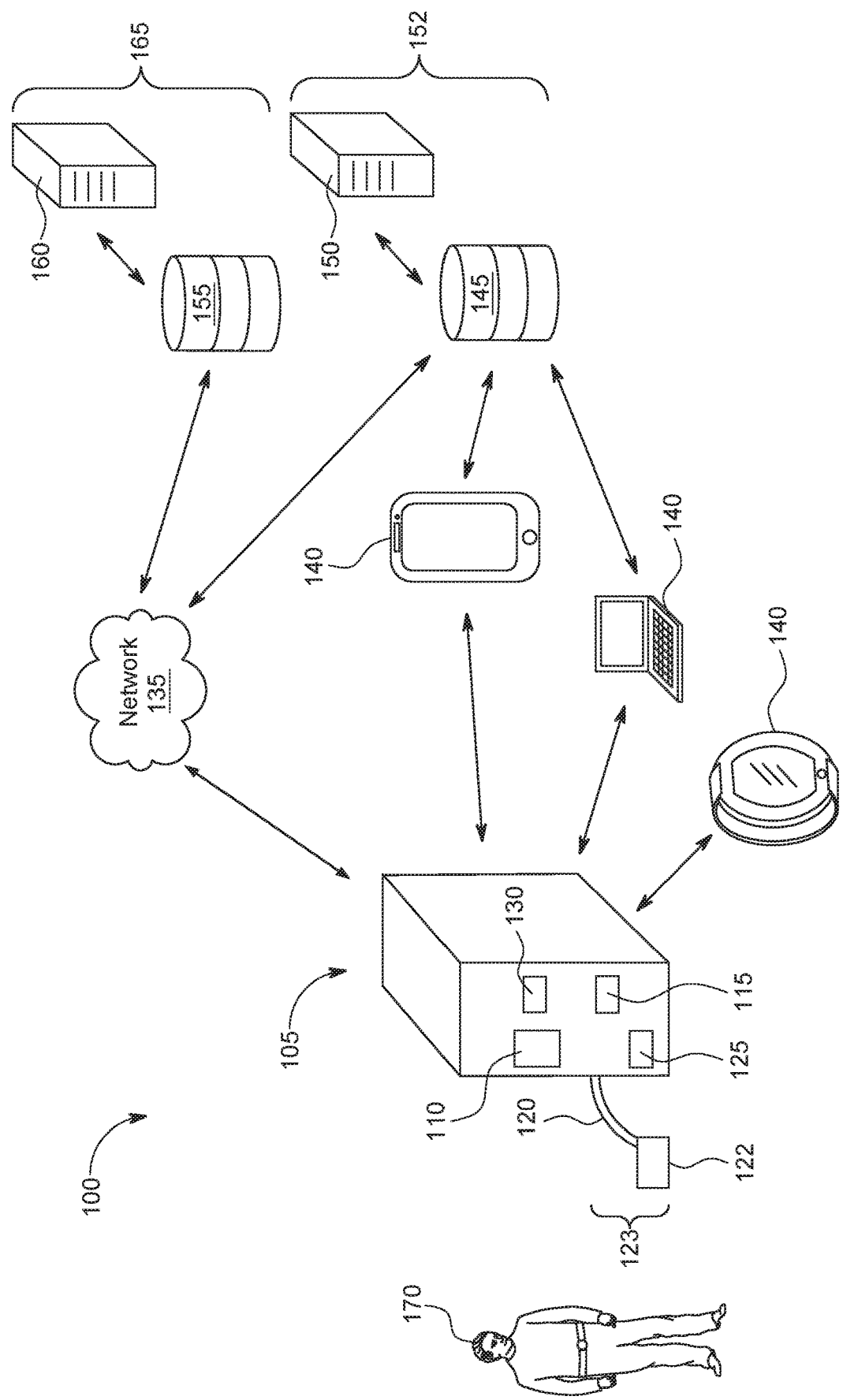
FIG. 1 illustrates a food preparation environment with a food system configured to prepare and dispense food in accordance with some implementations of the disclosed technology.

The disclosed technology relates to a food system configured to cut food, store food, cool food, heat food, serve food, mix food, prepare food, preserve food, monitor food inventory, juice food, recognize food or spoilage in the food, sanitize food, suggest meals, or compost food. To perform these operations, the food system can use a robotic arm, an antenna array, and containers that store the food. The food system can perform operations automatically based on a user's request or using data that predicts what a user wants or should eat to stay healthy.

In an implementation of the food system, the food system prepares a salad for a user based on the user requesting a salad via a user interface or a mobile phone. For example, a person can use his or her mobile device to communicate a desired salad recipe to the food system, where the food system can be located in the user's home or in a business location. The food system gathers vegetables from containers in the food system, cuts the vegetables using a water jet or robotic arm, gathers dressing and other ingredients for the salad recipe, mixes the salad, and provides the salad to the person. The food system can provide a salad portion that is in accordance with a user's desired health goals. For example, the food system can provide a small salad (e.g., less than 300 calories) if a user intends to lose weight or reduce the amount of saturated fat in the recipe if a user wants to avoid fat because of heart issues.

Also, the disclosed technology includes a method for removing spoilage from food items that will be included in a meal. The food system performs the method by receiving a request to prepare a meal; determining that the meal includes a food item available in a container of the food system; transmitting, by an antenna array, electromagnetic (EM) waves at the food item; measuring the reflection, refraction, or absorption of the EM waves; determining that the food item has a portion of spoilage and determining a location of the spoilage of the food item based on the measured reflection, refraction, or absorption of the EM waves; removing, with a robotic arm of the food system, part of the spoilage for the food item; and providing the food item with removed spoilage as a meal. The robotic arm can be configured to hold and use a knife, blade, or rotating blade to cut or remove spoilage.

In some implementations, the food system disposes of food waste in a self-contained composting unit physically coupled to the food system. Additionally, in some implementations, the food system monitors food inventory, keeps food sanitary, and provides a user with updates regarding the inventory.

In some implementations, the food system communicates with the Internet and mobile devices to enable customized food environment for a user. For example, the disclosed technology uses big data algorithms to optimize a user's diet based on learned and observed behavior (e.g., tracking caloric intake and exercise). The food system can also suggest shopping lists, food recipes, and online order execution. In some implementations, the food system uses location services to locally source and buy food for the recipes. The food system can adjust its algorithms based on the season, availability of food, price of food, and a user's health goals or budget.

Although a single food system can provide food to a user, in some implementations, the disclosed technology has multiple food systems and each food system can provide the same or different foods. With the multiple food systems, a user can order food based on proximity to a food system or based on a type of food offered at the food system. For example, the disclosed technology can include one food system in a building in a central city location that provides salads and another food system outside of the city center, where the other food system provides sandwiches or warm food. A user can view both food system locations on his or her mobile device and order food from a food system based on his or her location or food preference. Although two food systems are provided in this example, several (e.g., 10, 100, or even 1000s) of food systems can provided in different locations with same or different food choices.

The food system can be configured to periodically (e.g., every few minutes, daily, or weekly) scan containers within the food system to determine the inventory of the food system. The food system can also use this inventory to alert users that certain food items are not available or certain meals cannot be prepared because the food system does not have the necessary food item to make the meal (e.g., based on a recipe).

Food spoilage is a direct indication of its quality. Food spoilage occurs due to the microbial and enzymatic activities that change the composition of the food with their metabolites, thereby changing the dielectric properties of food. Dielectric properties of food are those electrical properties which measure the interaction of food with EM fields or waves. Dielectric properties of food can vary based on humidity or temperature. To calculate the dielectric properties of food various techniques can be used. For example, in *Analysis of Bread Dielectric Properties using Mixing Equations* publichsed by Journal of Food Engineering on Jan. 3, 2009, all of which is incorporated herein by reference, Yanhong Liu, Juming Tang, and Zhihuai Mao disclose techniques for measuring the dielectric of bread. As another example, Filiz Icier & Taner Baysal (2004) Dielectrical Properties of Food Materials—1: *Factors Affecting and Industrial Uses, Critical Reviews in Food Science and Nutrition*, 44:6, 465-471, which is incorporated herein by reference for its entirety, discloses factors for calculating dielectric properties of food.

The disclosed technology solves at least one technical problem related to healthy food with a food system that monitors the food and prepares the food to be healthy. Specifically, the food system can use an antenna array and or camera system to identify food spoilage and can also use a water jet, robotic arm, or string to cut away the spoilage. If the whole food item is spoiled, the food system can dispose of the spoiled food using an internal composting system. The food system can also customize a user's diet according to a user's goals (e.g., weight loss, weight gain, allergies, taste, budget, time to prep) and use this information to stock fresh and healthy food for the use. The food system also reduces the amount of time an individual must spend preparing food, shopping, and planning meals. Also, the food system helps a user eat healthy by monitoring the spoilage of food automatically and removing spoilage automatically.

A few definitions of terms follow in Table 1.

TABLE 1

| Term | Definition |
| --- | --- |
| Food | An edible item. Some examples of food include vegetables, seeds, fruits, wheat, or meat. Foods include solid, liquids, and gases. Food can be raw, unprepared, prepared, cooked, cleaned, uncleaned, or sanitized. Food can be warmed, cooled, frozen, or modified in other ways as described in this disclosure. Also referred to as "food item" when referring to a piece such as an apple, piece of lettuce, or piece of meat. |
| Ingredient | A substance that forms part of a mixture. An example of an ingredient is salt, sugar, or spice. |

Turning now to the Figures, FIG. 1 illustrates a food preparation environment 100 including a food system 105, network 135, computing devices 140, database 145 and server 150 (collectively "the backend food system" 152), and third-party database 155 and third-party server 160 (collectively "the third-party system" 165, where third party refers to a person or entity separate from a user). The food system 105 prepares food for a user 170 based on communication with the user 170, the computing devices 140, the network 135, and the backend food system 152 and the third-party system 165. For example, the food system 105 receives a salad recipe from the third-party system 165 and prepares a salad for the user 170. In preparing the recipe, the food system 105 can determine that the food system 105 has the ingredients and food items for the recipe. If the ingredients or food items are running low or missing, the food system 105 can notify the user 170 or automatically order more ingredients or food items via the network 135. Each of the components in the food preparation environment 100 is described in more detail below.

The food system 105 includes several interior and exterior components to interact with the user 170 and prepare a meal. The interior components are described in more detail in FIG. 9. Regarding the exterior components, the food system 105 includes a graphical user interface 110, a food dispensing area 115, a composting tube 120 and composting storage 122, (collectively "the compost system" 123), user insert 125, and payment interface 130. The graphical user interface 110 enables a user to communicate with the food system 105 via a touchscreen or pushing a button on the graphical user interface 110. Although a graphical user interface is shown in FIG. 1, a physical user interface with buttons can also be used as an interface between the user and the food system 105. In some implementations, the food system 105 does not have a graphical user interface and users communicate with the food system 105 solely based on wireless communication from a mobile device configured to communicate with the food system 105.

The food dispensing area 115 provides the user with food on a plate, in a bowl, in a cup, or other food carrying device. The compost system 123 composts food and is described in more detail in FIG. 8. The payment interface 130 enables a user to pay for the food using a credit card, mobile phone, or other payment method. The user insert 125 enables the user 170 to insert food into or remove food from the food system 105 (e.g., a space, door, glass door to enable a user to see if food is ready). For example, the user can input salt, a missing ingredient, his or her favorite food into the food system 105.

Although components are shown on the exterior of the food system 105, the components can be moved to the interior. For example, the payment interface 130 can be eliminated if the food system 105 is used at a residential location as compared to a commercial location. In some implementations, a camera, video camera, microphone, or speaker can be added to the food system 105 to further enable communication between the user 170 and the food system 105.

The food system 105 can identify the user 170 with facial recognition or a receive voice commands with a microphone (e.g., a user can ask the system to "order more tomatoes"). In some implementations, the food system 105 can use voice-recognition software (e.g., Siri™, Watson™, Cortana™) to determine what the user 170 wants to eat and when he or she wants to eat it.

The food system 105 can communicate with computing devices 140. The computing devices 140 are computing devices configured to communicate wirelessly or using a wired connection. Some examples of the computing devices 140 include a mobile phone, tablet computer, mobile media device, mobile gaming device, vehicle-based computer, wearable computing device, laptop, desktop, sensor, or other electronic device. For example, the food system 105 can communicate with a user wearing a smart watch, and the smart watch can transmit desired calorie intake for a user. If the user grants permission, the food system 105 can gather person information about the user (e.g., exercise habits, weight, height, age, health, and other attributes) to determine the type of food and amount of food the user should eat to stay health as described in FIG. 9. The computing devices 140 and the food system 105 can communicate using Bluetooth™, ZigBee™, Wi-Fi™, or another 802.11 Institute of Electrical and Electronics Engineers (IEEE) wirelessly communication standard. In some implementations, the computing devices 140 include an application (e.g., mobile app, web app, or other software) that enables a user to input information into the food system 105 or control the food system (e.g., turn it off while on vacation or turn it into a low-power mode).

The network 135 enables the food system 105 to communicate with other devices. In some implementations, the network 135 is a single network or multiple networks including one or more border networks, voice networks, broadband networks, service provider networks, Internet Service Provider (ISP) networks, and/or Public Switched Telephone Networks (PSTNs), interconnected via gateways operable to facilitate communications between and among the various networks. The network 135 can include communication networks such as a Global System for Mobile (GSM) mobile communications network, a code/time division multiple access (CDMA/TDMA) mobile communications network, a 3rd or 4th generation (3G/4G) mobile communications network (e.g., General Packet Radio Service (GPRS/EGPRS)), Enhanced Data rates for GSM Evolution (EDGE), Universal Mobile Telecommunications System (UMTS), or Long Term Evolution (LTE) network), or other communications network such as a Wireless Local Area Network (WLAN). Although the food system 105 can use the network 135 to communicate with other devices, the food system 105 can communicate locally with devices using wireless communication protocols such as Bluetooth™ or ZigBee™; and the food system can also use near-field communication (NFC).

Using the network 135, the food system 105 can communicate with the backend food system 152 and the third-party system 165. The backend food system 152 enables the food system 105 to communicate with the manufacturer or technical support for the food system 105. The backend food system 152 can diagnosis, fix, and trouble shoot problems for the food system 105 automatically without contacting the user 170. The backend food system 152 updates the food system 105 too. The third-party system 165 can be a business or organization related to food. For example, the third-party system 165 can be Amazon Fresh™ or other grocery service. The third-party system 165 can provide the food system 105 with the location and price of food items in that are close (e.g., within 5-10 miles) of the food system 105.

The food preparation environment 100 can be located in different environments. In some implementations, the food system 105 is in a restaurant, school, cafeteria, remote military, or business location. Although a single food system 105 is shown in FIG. 1, the food preparation environment 100 can include several food systems 105.

The food system 105 can be custom designed to serve a type of food (e.g., salad, sandwich, pasta, Italian, or Chinese). In such implementations, the food system 105 can display advertisements for such food electronically or with physically coupled signage. Given the location and amount of food demanded, the food system 105 can vary from a small refrigerator to a large industrial refrigerator.

Figure 2:
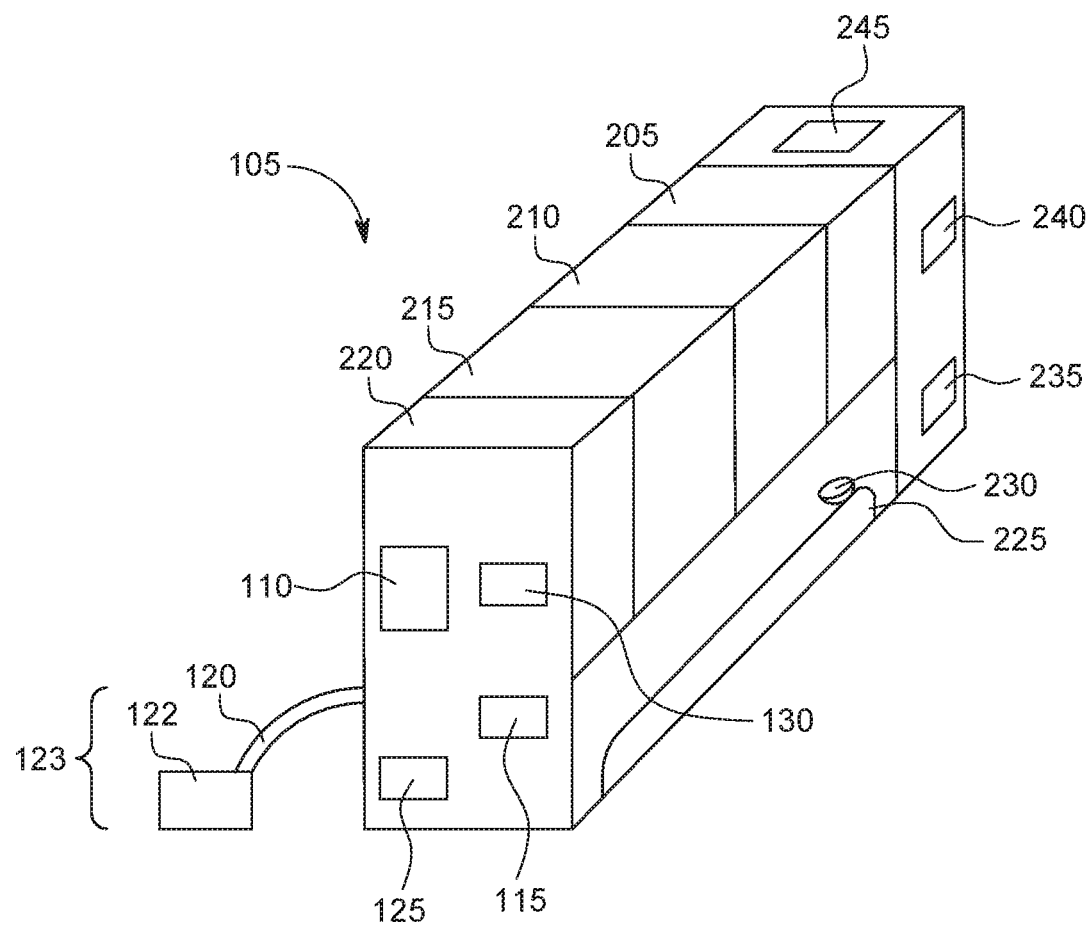
FIG. 2 is a block diagram illustrating the food system from FIG. 1 in more detail in accordance with some implementations of the disclosed technology.

FIG. 2 is a block diagram illustrating the food system 105 from FIG. 1 in more detail. The food system 105 is configured to: store food, wash food, recognize food, cut food, juice food, identify spoiled or expired food or food portions, remove the identified portions, weigh food, calculate caloric values of food, mix food and ingredients, sanitize the food, dispense, cook food, modify the temperature of food, or serve food.

To enable these functions, the food system 105 has a pantry architecture with four stations: raw material station 205, preparation station 210, ingredient station 215, and dispensing station 220. Although four stations are shown in FIG. 2, the food system 105 can include than four stations depending on desired food type or dispensing capability of the food system 105. For example, the ingredient station 215 and dispensing station 220 can be combined into one station to reduce the size of the food system 105. Each of the four pantry stations can include a set of drawers and container bins configured to hold the ingredients or food. Each station is described in more detail in FIGS. 3A-3C, and as noted above the food system can have more than four stations (e.g., 5, 6, 7, or more) or less than four stations (e.g., 1, 2, or 3).

Continuing with FIG. 2, the food system 105 also includes a track 225, a bowl 230 positioned on the track to move food or ingredients from station to station, a temperature control unit 235 to regulate the temperature of the food system 105, a food carrier dispensing unit 240, and power unit 245 (e.g., a power circuit electronically coupled to a power outlet). In some implementations, the power unit can include an uninterruptable Power Supply (UPS) that is cooled continuously by the temperature control unit 235. Although FIG. 2 includes one track 225, one bowl 230, one temperature control unit 235, one food carrier dispensing unit 240, and one power unit 245, the food system 105 can include many of these components. For example, the food system 105 can have multiple power units 245 where each unit is dedicated to power a different component of the food system 105. The food system 105 can also have multiple temperature control units 235, where temperature control unit controls the temperature of different areas (e.g., storing different food types or measuring temperature in each container).

Figure 3A:
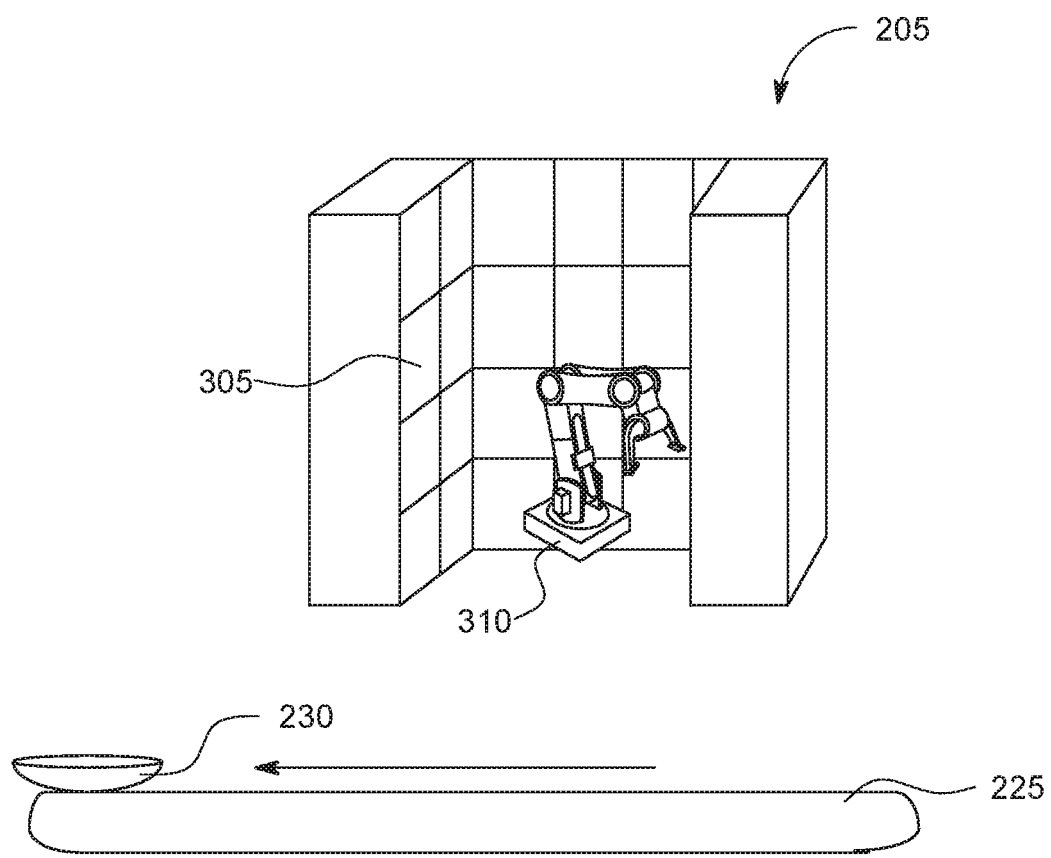
FIGS. 3A-3C are block diagrams illustrating components of the food system from FIG. 2 in more detail in accordance with some implementations of the disclosed technology.

FIG. 3A discloses the raw material station 205 in more detail. The raw material station 205 includes containers 305 and a robotic arm 310. In some implementations, the robotic arm 310 can place food in the bowl 230 and the track 225 can move the bowl 230 right to left (or vice versa) because the track 225 is a powered mechanically rotating track. The food system 105 (see FIG. 9) controls the robotic arm 310, and the robotic arm 310 can move, pick up, smash, push, pull, rotate, or move food items or ingredients. In some implementations, the robotic arm 310 can include a blade, rotating blade, a string with tension, or other device configured to cut a food item.

The containers 305 store food or perform operations on food. The operations performed on food are described in FIGS. 4A-4C, 5, and 6. Some of the operations include: cleaning, cutting, sanitizing, weighing, storing, cooling, detecting the type of food, and detecting the condition of the food or portions of the food. The containers 305 can vary in size and type and can be detachable from the food system 105. For example, the container 305 can be one gallon to a pint in size, the containers 305 can also be shatter and heat resistant material or composed of material that reduce bacteria, fungus, or viruses (e.g., antimicrobial material copper or titanium dioxide). The containers 305 can be surrounded by insulation to regulate the temperature of the container and the contents of the container. For example, some containers 305 can be used for keeping food warm, other containers can be used for keeping food cool. The containers 305 can store food such as: lettuce, carrots, tomatoes, onions, garlic, other vegetables, meat, noodles, fruit, granola, bread, or other desired food items or condiments.

One advantage of the containers 305 in the food system 105 is that each food item can be stored at different conditions (e.g., hot, cold, freezing, warm, moist, dry, room temperature). Additionally, a technician can easily fix a malfunctioning container by replacing the container rather than a large portion of the food system 105. For example, a container configured to keep lettuce cool may malfunction and become warm, the technician can replace the container without disrupting other containers. Additionally, users can customize the containers to their needs. Restaurant owners can request the food system 105 to have containers to a food type (e.g., Italian, Chinese) or conditions (e.g., warm, cold, large, small).

The containers 305 have a schematic numbering system to enable the robotic arm 310 to systematically access, use, and modify the contents of the containers 305. Each wall of the raw material station 205 can have a different number of bins and drawers with a different number of containers. In some implantations, the raw material station 205 has 32 drawers, where each drawer contains 12 containers. The food system 105 addresses a desired container by a hierarchy of the station, the drawer, and the container codes to locate desired material. For example, raw material station 205 addresses code would break down as follows: 2153313—this means reading the numbers left to right raw material station 205, drawer row 3 column 3, bin row 1, column 3. The first number directs the programmed driver response to the action initiating station and the last four numbers are common to pantry locations. Each container 305 can also information about the container stored in memory (see FIG. 9). As an example, the table below includes representative information about the food system 105 and its containers, where the raw material station 215 (the first number in a bin location) and the drawer location (e.g., 12) describes the food. The number of drawers can vary based on the type of food or size of food stored in the food system

TABLE 2

Example Container Contents and Conditions

| Bin Location | Content | Condition | Estimated expiration | Weight | Temperature |
|---|---|---|---|---|---|
| (205, 12) | Apple | Good | 3 days | .2 lbs. | 50° F. |
| (205, 16) | Lettuce | Great | 5 days | .8 lbs. | 50° F. |
| (205, 01) | Tomato | Poor | Less than 4 hours | .1 lbs. | 50° F. |
| (205, 22) | Cheese | Good | Two weeks | 1 lbs. | 60° F. |

Using lookup tables such as example Table 2 above, the robotic arm 310 can receive instructions to prepare a salad and gather each item for the salad from different containers 305 in the raw material station 205. The robotic arm 310 can place each item of the salad in the bowl 230, and the track 225 can move the bowl from the raw material station 205 to the ingredient station 215 for further food preparation.

Figure 3B:
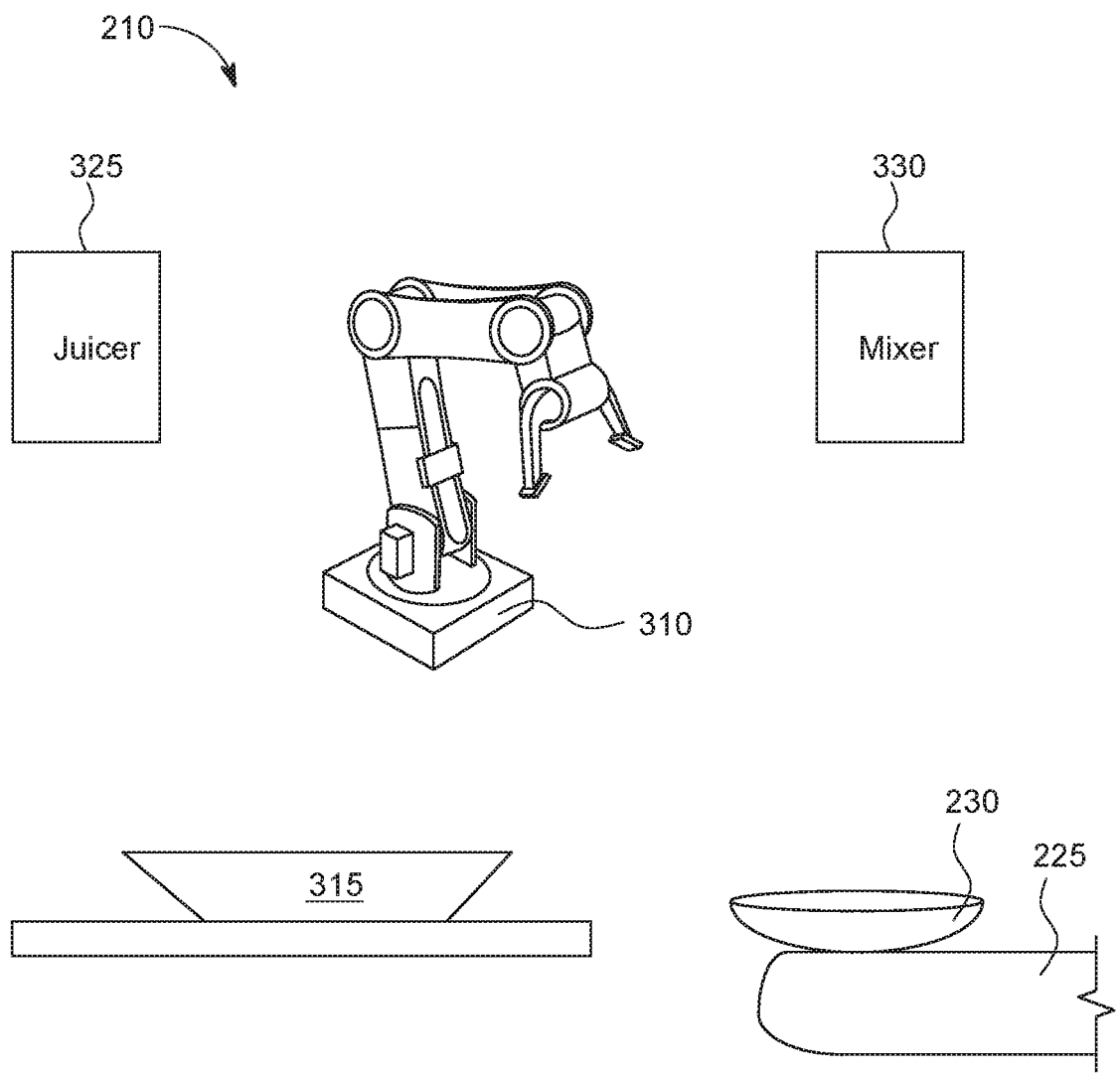

Moving to the next station, FIG. 3B describes preparation station 210 in more detail. FIG. 3B includes the robotic arm 310, the track 225, the bowl 230, cooking platform 315, juicer 325, and mixer 330. Although not shown in FIG. 3B, the station 210 can also include containers 305.

The cook platform 315 cooks the food in combination with the robotic arm 310. The cooking platform can heat food placed on it, cool food placed on it, shake food placed on it, or cause food to boil or freeze. For example, the cooking platform 315 can be a metal stove top that heats up or a refrigerated plate that cools food. In some implementations, the robotic arm 310 can wipe food off the cooking platform 315 into the composting system (described in FIG. 8). The cooking platform 315 can be configured to open to enable food that is unused or leftover to fall into the composting system. The robotic arm 315 can use the cooking platform as a surface to cut, spray, wash, dice, or otherwise modify food or ingredients placed on the cooking platform.

The juicer 325 and the mixer 330 can be used to process food. The juicer 325 can be a blender, juicer, food processor, or other electronic device that enables the process or cutting a food item such that the food item because a juice substance. In some implementations, the juicer 325 can add ingredients (e.g., water) or other food products to change the consistency of the food time that is being processed or juiced. The mixer 330 can mix a food item or mix multiple food items. The mixer 330 can include an electronic mechanical unit to move food items or otherwise mix food items. The robotic arm 310 can place food items in the juicer 325 and the mixer 330 and remove items from these components. In some implementations, the robotic arm 310 processors foot items in the juicer 325 or the mixer 330 before a user requests the food to have the food ready in advance (e.g., if the system determines that a user is returning from a workout and will likely have a protein drink).

Figure 3C:
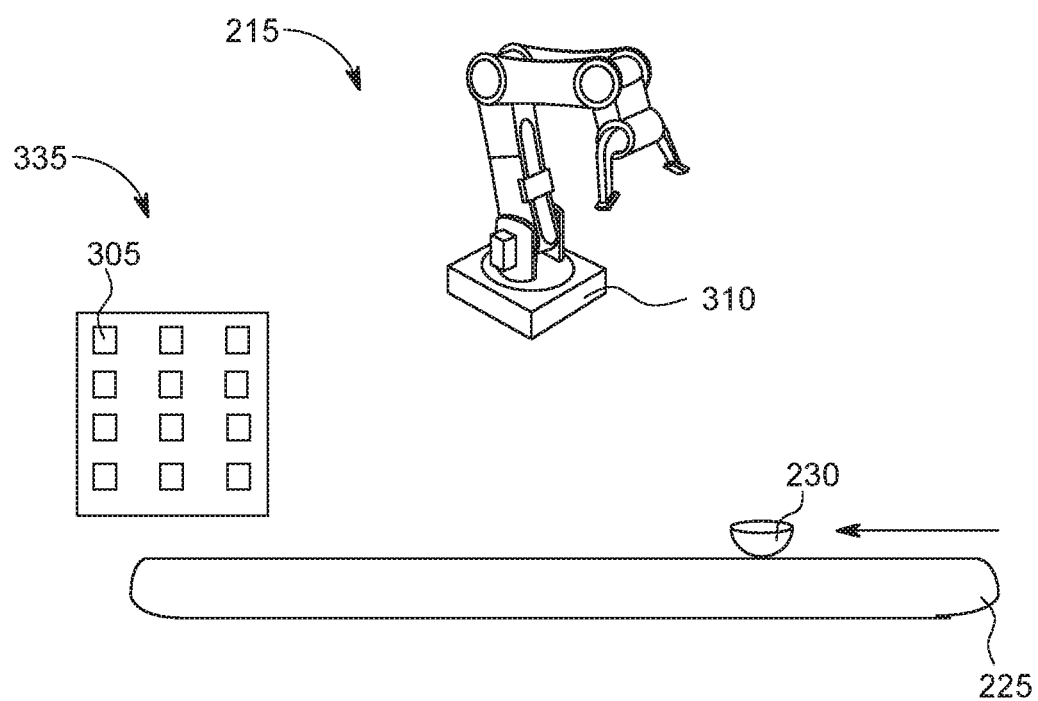

Moving to the next station, FIG. 3C describes ingredient station 215 in more detail. FIG. 3C includes the robotic arm 310, the track 225, the bowl 230, and the ingredient dispensing unit 335. The ingredient dispensing unit 335 is described in more detail in FIG. 8. In general, the robotic arm 310 adds ingredients to the bowl 230 units that are available in the ingredient dispensing unit 335. The robotic arm 310 or the track 335 can send the bowl with a fully prepared meal to a user at the dispensing station 220. The dispensing station 220 can be a cool area or storage area where the food waits until a user is ready to receive it. The dispensing area is accessible to the user 170.

Figure 4A:
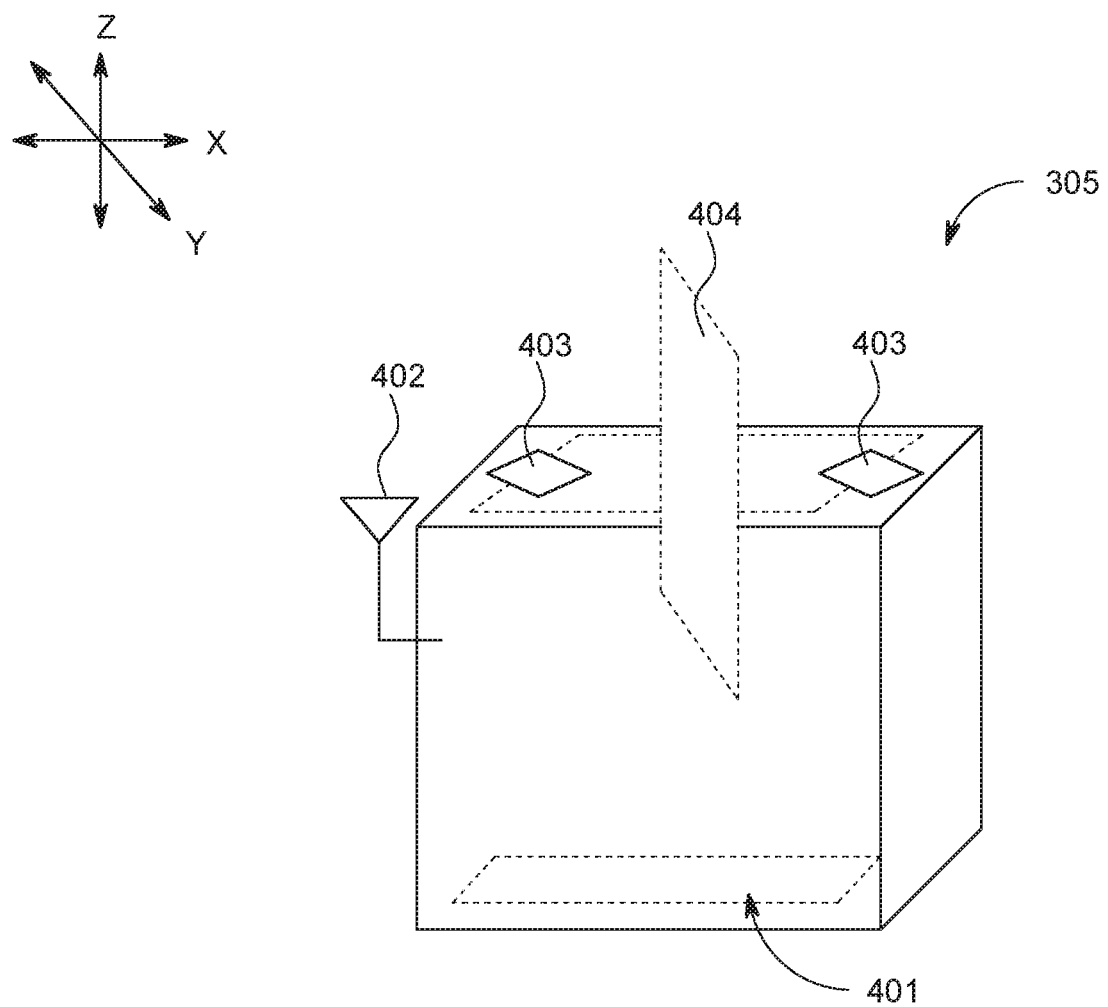
FIGS. 4A-4C are block diagrams illustrating container components of the food system shown in FIG. 2 in accordance with some implementations of the disclosed technology.
Figure 4B:
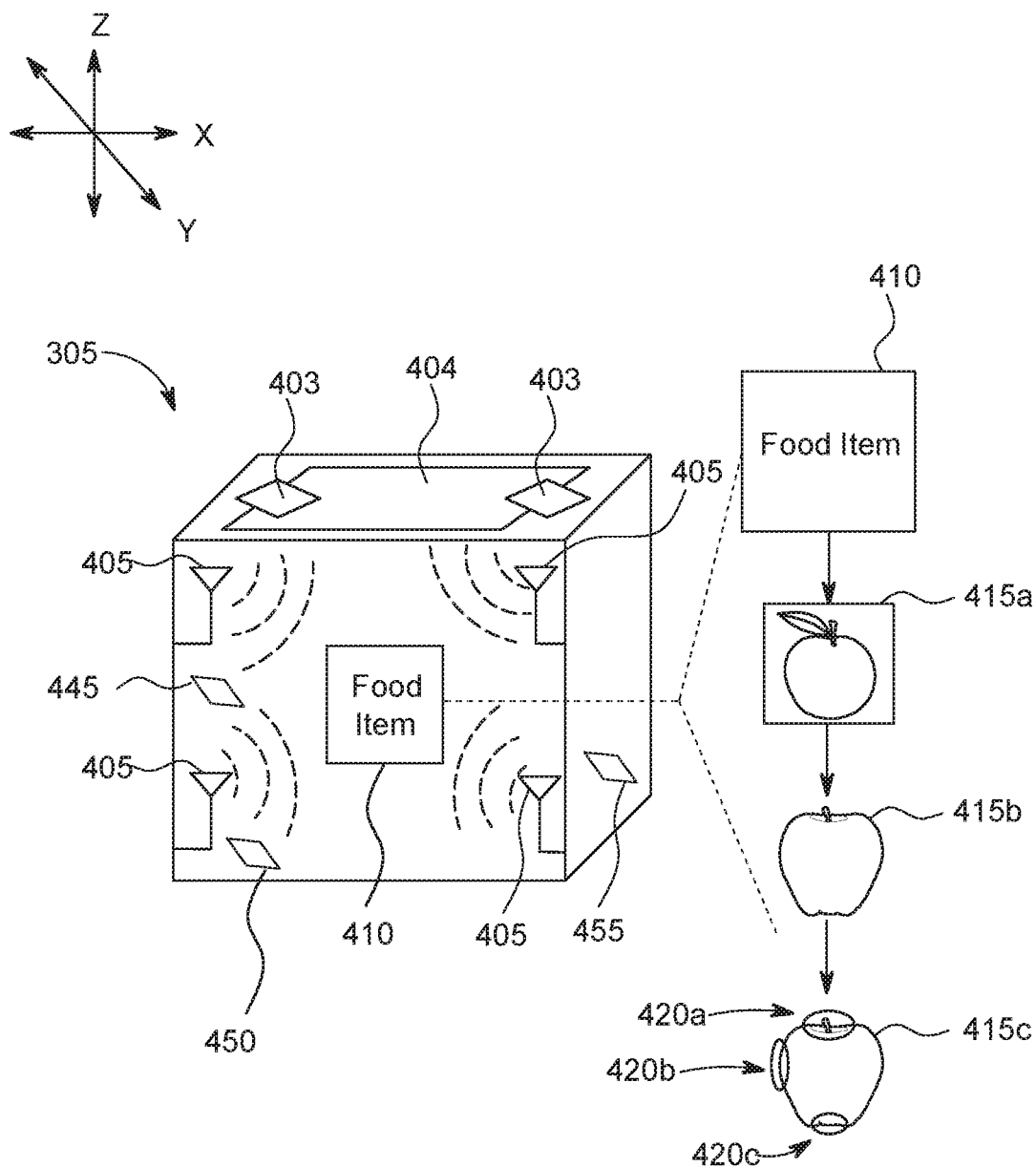
Figure 4C:
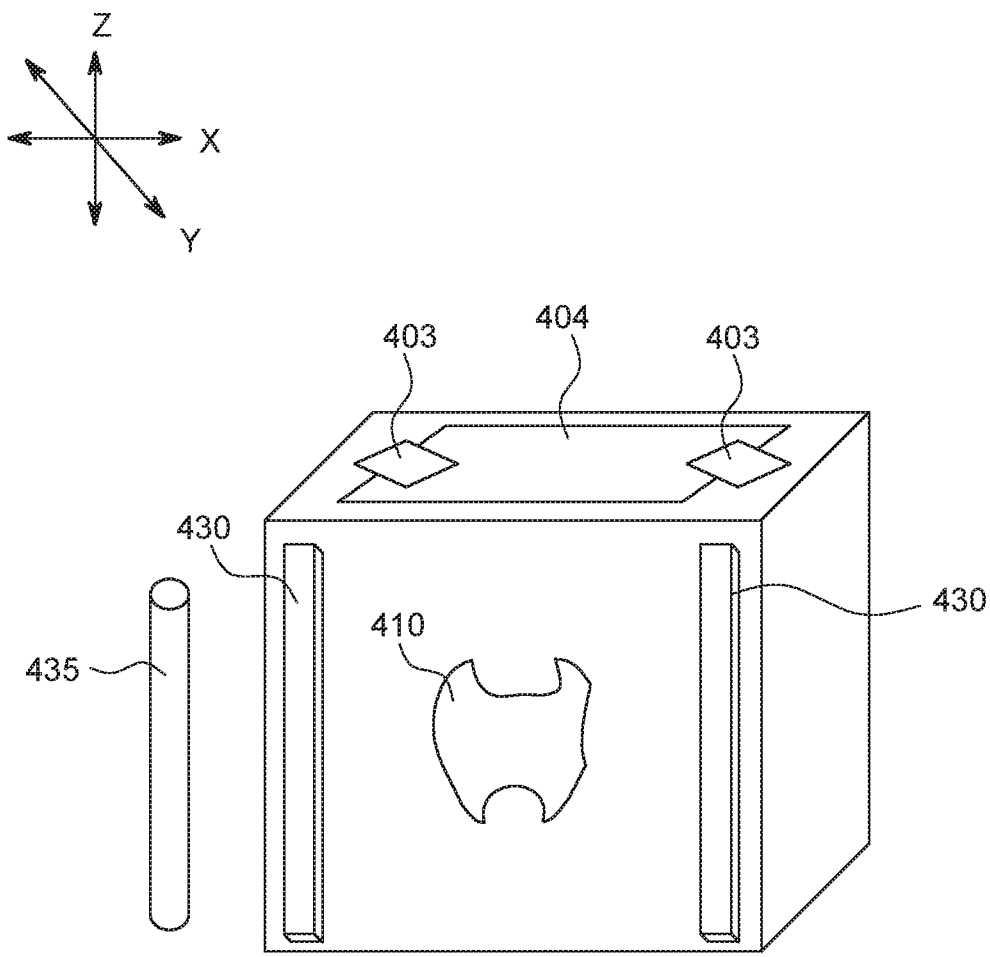

FIGS. 4A-4C are block diagrams illustrating different types of containers 305. FIG. 4A discloses the container 305 configured to weigh and communicate information regarding contents of the container 305. The container 305 includes a scale 401, antenna 402, latches 403, and lid 404. The scale 401 can weigh the contents of the container 305. Some examples of scales include a mechanical scale, digit scale (e.g., with a stain gauge), an electronic device scale (e.g., based on microbalance circuits or small electronic sensors). The scale can be an internet of thing device (IoT device) such that it communicates weight information to other components of the food system or can communicate weight information wirelessly to other devices.

Although not shown, each container can include a small battery or power connection as part of a communication circuit to receive and transmit information. In some implementations, the container 305 does not include an antenna and rather includes a hard-wired connection for communication with the food system 105. The container 305 also includes the latches 403 and the lid 404. The latches 403 can be magnetically, electronically, or mechanically opened and closed to all access to the food. The food system 105 can control the latches 403 to open and close on command. In some implementations, the latches 403 and the lid 404 form an air-tight seal to keep food stored for long periods of time.

FIG. 4B discloses an object recognition container 305 configured to perform object recognition of a food item (collectively an "object recognition" system) and distinguish features of the food item 410. The object recognition system includes antennas 405 (collectively "the antenna array"), the food item 410, the latches 403, the lid 404, a temperature sensor 445, a detection unit 450, and a camera 455 (e.g., configured to take pictures of the food item). The food system 105 can use the camera and digital image processing algorithms that are stored in memory to identify food items. In some implementations, the food system 105 can store images of known food items and use those images to train or identify other food items. For example, the food system 105 can store a library of food item images. The object recognition system can identify different parts of the food item 410, the different parts can be 420a, 420b, and 420c. An apple is shown in FIG. 4B, but another food time can also be placed in the container 305. Also as shown in FIG. 4B, the object recognition system can analyze different images or datasets 415a, 415b, or 415c to determine the location of spoilage, where each image or dataset includes information related to EM wave properties of the food item.

The antennas 405 are configured to transmit EM waves at the food time 410. In some implementations, the container 305 includes an array of the antennas 405 where some antennas transmit microwave radio frequency (RF) waves at one frequency and other antennas transmit microwaves at another frequency. For example, one frequency is designed to penetrate the food item (e.g. skin of the fruit) and the other does not. The food system 105 can compare the data from the two signals based on the two frequencies to allows clear differentiation of an object's characteristics; for example, the container 305 also has detection units that detect return signals (e.g., reflected). Frequencies can be varied depending on the food. In some implementations, 2 GHz to 20 GHz (or more such as 96 GHz) are used and frequencies that are safe for humans and food. In some implementations, both frequencies may undergo continuous modulation. And a third frequency may be used to differentiate between different types of items. The antenna array can use microwave frequency waves or radio frequency waves. The antenna array is a linear array, circular array, and planar array.

In some implementations, the antenna array is configured to emit electromagnetic waves that limit the amount of heat a food item will absorb such that the food is not cooked or damaged in order to preserve its taste. The antenna array can do this based on a time and/or frequency selection. For example, the antenna array can use shorts bursts or energy to avoid heating food, where the bursts of energy are spread over time to avoid heating the food (e.g., allowing it to cool down between bursts). The antenna array can also be configured to use frequencies that do not heat a food item such that the food item chemistry is changed by cooking or heat (e.g., not microwave frequencies that are used to warm food). The antenna array can determine a time burst or frequency based on the type of food, e.g., for foods with a lot of water the antenna array can be configured to use frequencies that reduce the amount of water resonance.

The temperature sensor 445 is configured to measure the temperature of the container or measure the temperature of the food item. The temperature sensor 445 can be a negative temperature coefficient (NTC) thermistor, a resistance temperature detector (RTD), thermocouple, semiconductor-based temperature sensor, or a laser based temperature sensor. The temperature sensor 445 can provide temperature information to the food system and the food system can use this temperature information in calculations regarding the food time (e.g., to determine the dielectric properties or expected absorption, reflection, or refraction of EM waves on the food item. The detection unit 450 is configured to measure reflection, absorption, or refraction of the EM waves by the food item. In some implementations, the detection unit 450 is included to measure EM waves and in other implementations the food system does not have the detection unit 450 and the antennas receive reflected or refracted EM waves to measure how the food item response to EM waves.

Like FIG. 4B, FIG. 4C discloses an object recognition container 305; however, the FIG. 4C uses microwave/magnetic fields to determine the condition of the food item 410 compared to the use of electromagnetic waves or radiation in FIG. 4B. The object recognition system includes antennas 405, the food item 410, the latches 403, the lid 404, the magnetic bar 430, and the magnetic field creator 435. The magnetic bar 430 and the magnetic field creator 435 in combination with an electrical current and detector and detect of a magnetic field changes based on the food item 410 in the container 305. Using the magnetic field properties, the container 305 can determine features of the food item. For example, the food item 410 is composed of different parts (e.g., skin, spoiled spots) and the difference in magnetic properties between these parts can be detected by the container 305.

An antenna array, physically or synthetically formed, can be used for reconstructing dielectric images, which has enriched the special area of microwave sensors measurement and enabled possibilities of dielectric construction of the object under test. The antenna array based microwave sensor can be used for both reflection and transmission mode measurement. The commonly used designs are linear array, circular array, and planar array.

Figure 5:
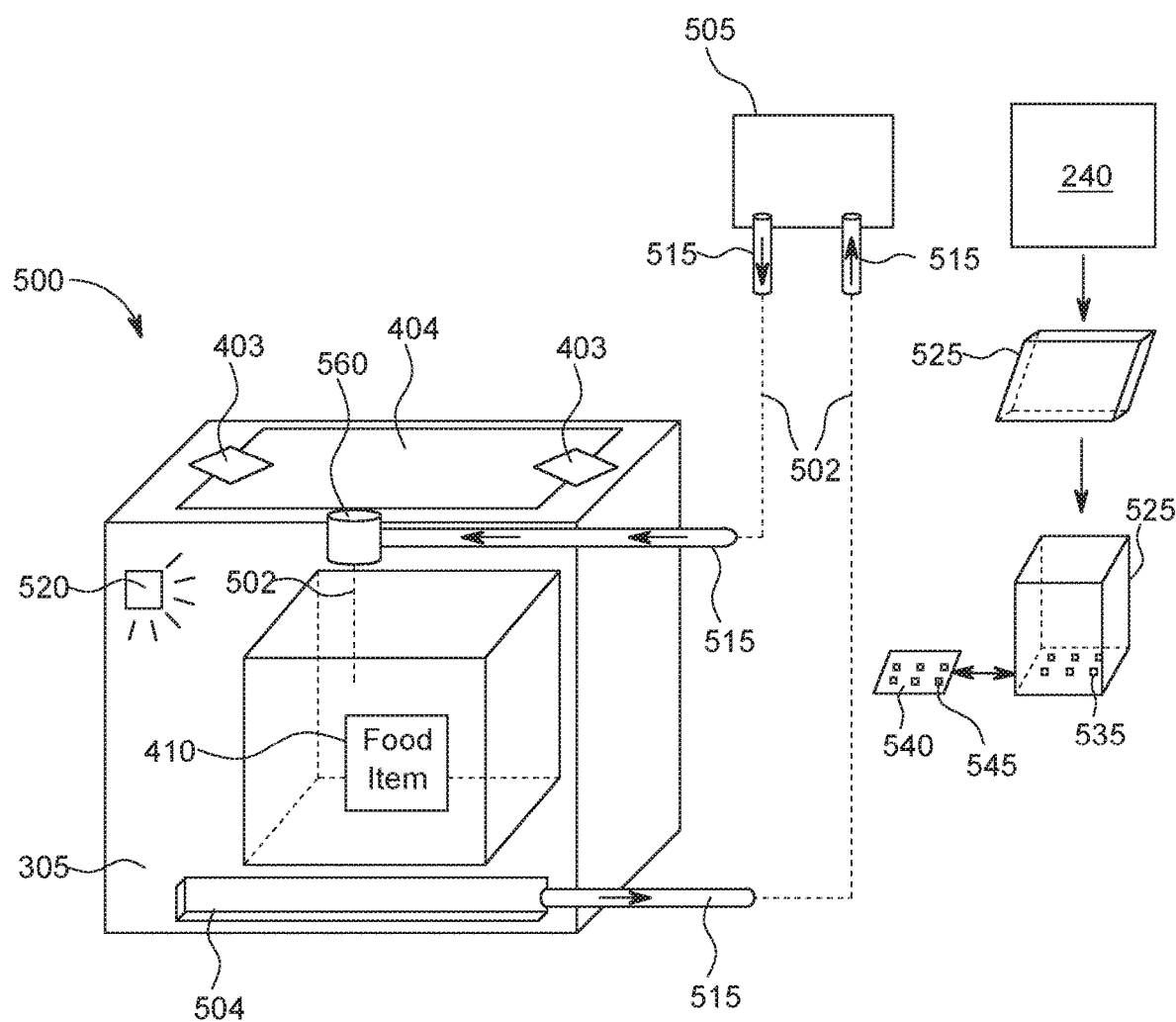
FIG. 5 is a block diagram illustrating components of the food system to sanitize, wash, and dispense food carriers in accordance with some implementations of the disclosed technology.

FIG. 5 is a block diagram illustrating a washing component, cutting component, and container dispenser component for the food system. The washing component 505 is a system that filters water through a container or through a dedicated washing area 500, and the water is used to clean the food item. The water 502 travels through a piping system 515, where the piping system has an inlet and outlet (also referred to as "the internal water system"). As shown in FIG. 5, the water exits the washing component 505, goes through a pipe, enters a container with a food item, and the exits the container. The washing system 505 can include a filter component 505 to filter or remove debris from the water 502. The filter can be a membrane filter, ion exchange filter, or other water purification system. Although the water 502 is shown in FIG. 5, other fluids such as salt water or citrus water can be used to clean the food item 410.

In addition to using water to clean the food item 410, the container can also use an ultra violet (UV) light 520 to sanitize the food item 410. In some implementations, the UV light 520 can be used in combination with the system described in FIGS. 4B and 4C so that light can be focused on locations of the food item that are more likely to contain an unsanitary portion of food.

Continuing with FIG. 5, a container can include a water jet 560. The water jet 560 can be used to cut the food item 410. The water jet can be physically coupled to the container with a metal beam or guide rail system, and the water jet 560 can move along the beam system so that it can cut the food item 410 in different locations. In some implementations, the water jet 560 has multiple outlets and each outlet can spray or eject water at different pressures. The water jet 560 is generally configured to eject water at pressure that is strong enough to cut food, but not too strong so that the food is damaged. The water jet 560 can vary its water pressure based on the type of food. For example, the food system 105 can determine that a strawberry is container in the container, and the food system 105 can send instructions to the water to cut the strawberry at a water pressure that cuts the strawberry without damaging it. The food system 105 can use the techniques described in FIGS. 4B and 4C to identify the food item or portions of the food item 410 and adjust its water pressure output accordingly (e.g., low water pressure for soft items or high depending on desired precision).

The food carrier dispensing unit 240 dispense bowls or food carrying containers. The food carrier dispensing unit 240 includes a food carrier 525 that is composed of a biodegradable paper that folds. The food carrier 525 can be stored as a flat object and then opened (e.g., by dropping it) so that the container forms a box or box-like structure. The food carrier 525 can store food and then be disposed of in an environmentally friendly manner. The food carrier 525 can also include holes 535 (e.g., perforations) at the bottom of the food carrier 525 so that fluids (e.g., unwanted fluid) can be drained out the bottom. In some implementations, the food carrier 525 is paired with a bottom plate 540 with hole fillers 545, where if the bottom plate 540 is inserted into the food carrier 525, the bottom plate 540 blocks the holes 535 of the food carrier 525.

Figure 6:
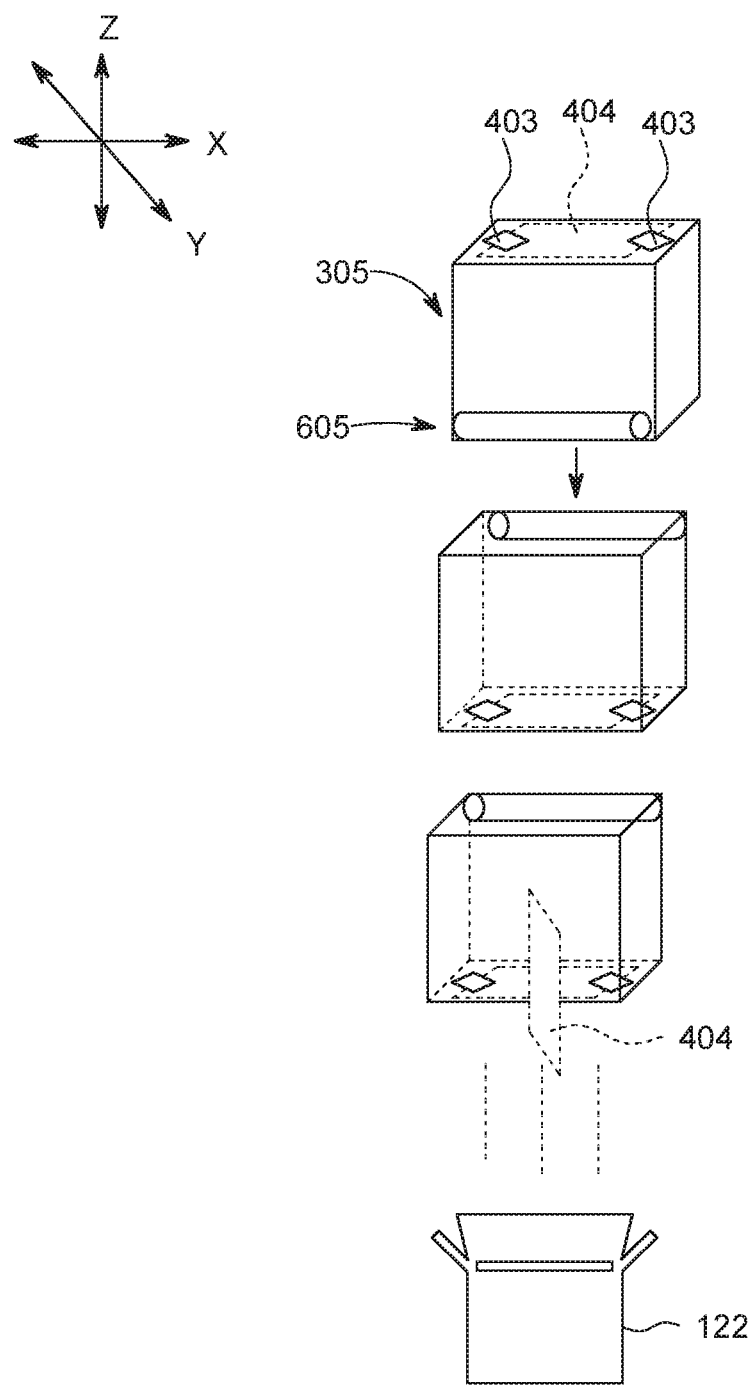
FIG. 6 is a block diagram illustrating a container rotating in accordance with some implementations of the disclosed technology.

FIG. 6 is a block diagram illustrating rotation of a container component of the food system. FIG. 6 includes the container 305 that has the latches 403 and the lid 404. FIG. 6 also includes a rotation bar 605. In some implementations, the rotation bar is a piece of metal with magnetic properties such that a magnetic field can be applied to the container to rotate it. In other implementations, the rotation bar 605 is just an indication of a rotation access that where the robotic arm 310 can rotate. As shown in FIG. 6, the container 305 can be rotated 180 degrees to empty out the container 305. The contents of the container 305 can be emptied into a food dispensing unit or a composting unit 122. For example, the robotic arm 310 (FIG. 3) can rotate the container to dispose of expired food.

Figure 7:
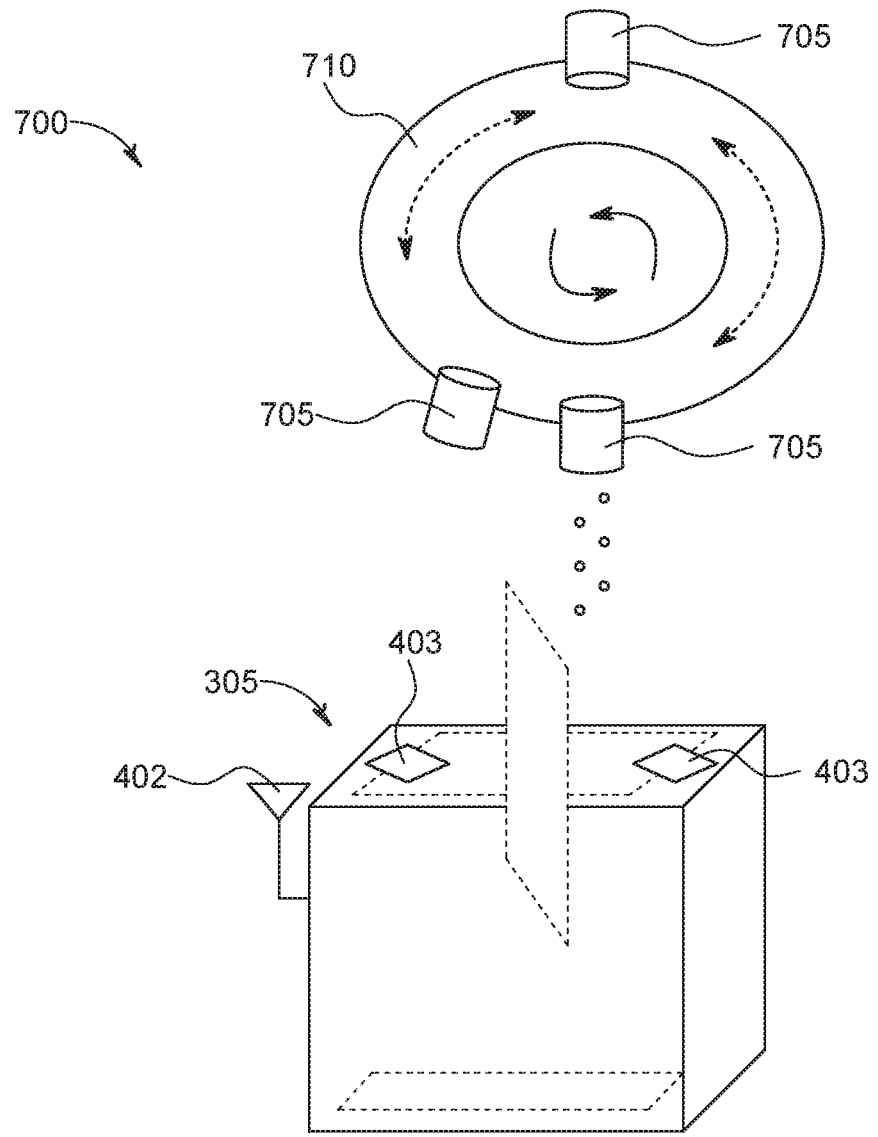
FIG. 7 is a block diagram illustrating an ingredient dispensing system for the food system in accordance with some implementations of the disclosed technology.

FIG. 7 is a block diagram illustrating an ingredient dispensing system for the food system. The ingredient dispensing system 700 includes an ingredient container 705 and a rotation belt 710 (also referred to as a "rotational ingredient belt"). Each ingredient container 705 contains ingredients. Some examples of ingredients include oil, salt, sugar, spices, herbs, pepper, and other natural substances used to flavor food. As shown in FIG. 7, the rotation belt 710 rotates (e.g., spins) around until a selected ingredient container 75 is positioned above the container 305, and then the ingredient container 705 dispenses an ingredient (e.g., salt).

Figure 8:
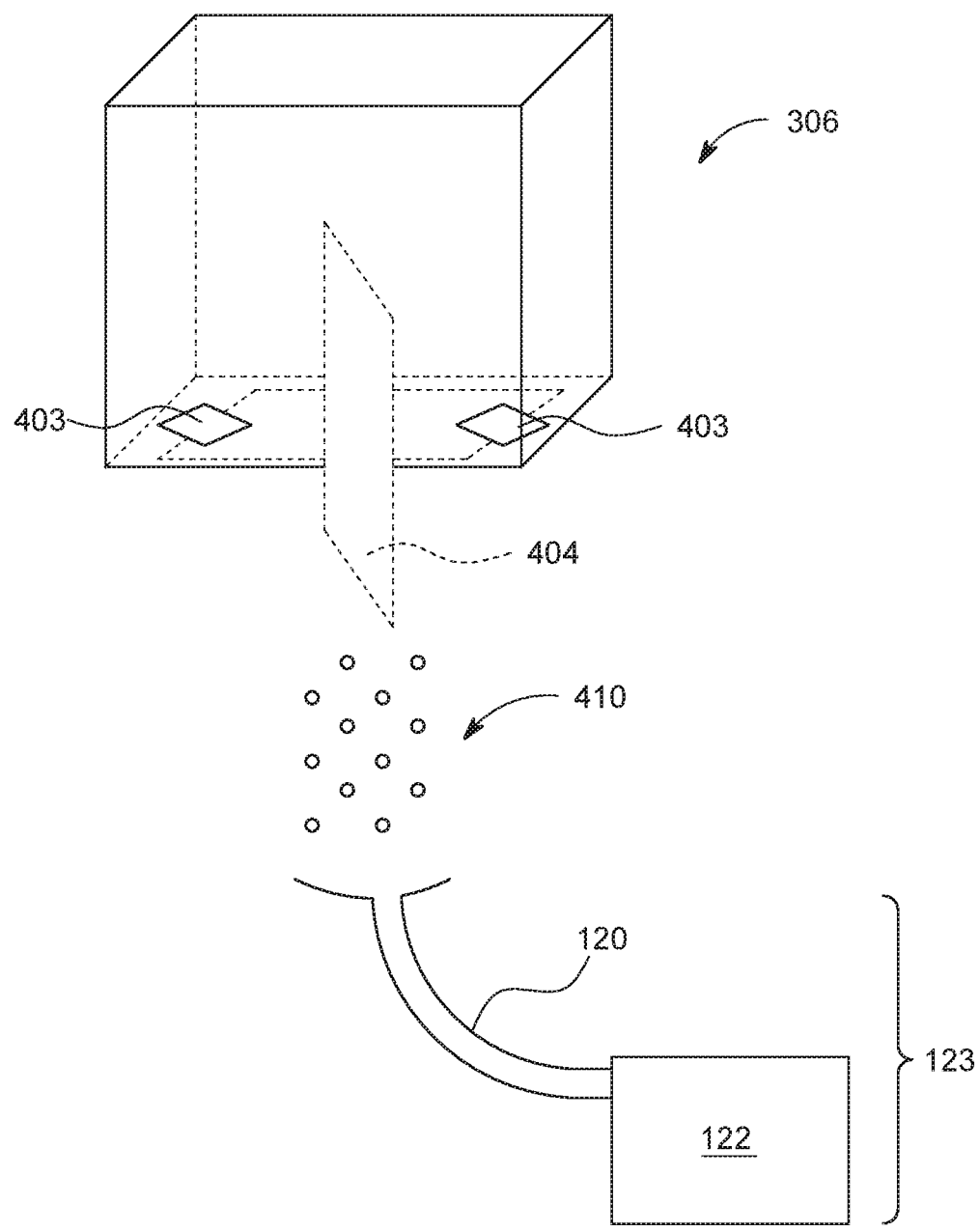
FIG. 8 is a block diagram illustrating a composting component for the food system in accordance with the disclosed technology.

FIG. 8 is a block diagram illustrating composting for the food system. The composting system 123 includes the composting tube 120 and the composting unit 122 (collectively "the composting system 123"). The container 305 that contains food waste can be rotated (e.g., so the lid 404 is on the bottom) and the latches 403 can be opened (e.g., by a magnet) so that food waste or compost in the container falls into the composting tube 120 and then into the compost unit 122. In some implementations, the robotic arm 310 rotates the container 305 and moves it close to the composting tube 120 to empty the container. In other implementations, the composting tube 120 is a dedicated compost container and all food waste is placed inside of it and stored there until the food system determines (e.g., by weight or a sensor) that it needs to empty the container 305. The food system 105 can empty a container periodical (e.g., every day or every week) or sporadically (e.g., based on user command or sensing a weight maximum).

The composting system 123 can include components (e.g., the composting unit 122) for improving the composting process. The compost system 123 can include a water jet to clean a container, chemicals to reduce the smell or compost or speed up the composting process (e.g., bacteria, fungus, acid, etc.). The composting unit 122 can be configured to detach from the food system 105 so that a user or machine can move it to another location or replace with an empty compost unit. In some implementations, the composting unit 122 is recyclable system or reusable in that a user can replace the composting unit 122. The composting unit 122 can also include a ventilation (e.g., perforated holes or an air flow system) to rotate the compost. The composting unit 122 can also into a stirring rod to mix the food waste inside the composting unit 122.

Figure 9:
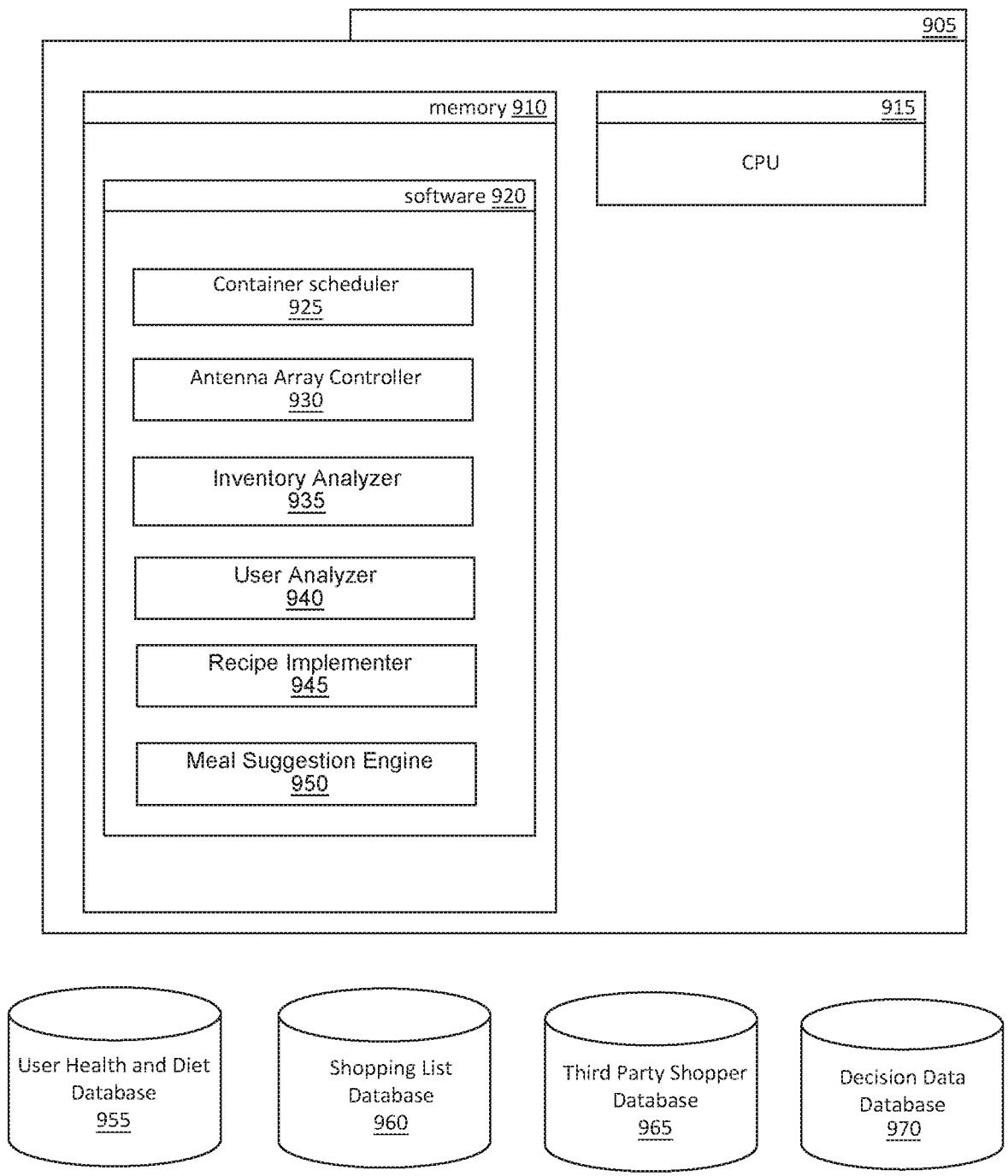
FIG. 9 is a block diagram illustrating components of the food system in FIG. 1 in more detail in accordance with some implementations the disclosed technology.

FIG. 9 is a block diagram illustrating interior components of the food system in FIG. 1 in more detail. The food system 105 includes hardware and software components to operate the food system 105. The components are collectively referred to as the food system central unit (FSCU). The FSCU 905 includes a memory 910, software 920, and a central processing unit (CPU) 915. The memory 910 stores instructions for executing software 920. The memory 910 stores software 920 comprised of one or more modules and data utilized by the modules. The software 920 performs certain methods or functions and can include components, subcomponents, or other logical entities that assist with or enable the performance of some of these methods or functions. The software 920 includes a container scheduler 925, antenna array controller 930, inventory analyzer 935, user analyzer 940, recipe implementer 945, and meal suggestion engine 950. This software can also communicate with: user health and diet database 955, shopping list database 960, third party shopper database 965, and decision database 970.

The container scheduler 925 can monitor, modify, and adjust the containers. The container scheduler 925 tracks all containers using the numbering system described in FIG. 3A and Table 2. The container scheduler 925 can instruct the robotic arms 310 (FIGS. 3A-3C) where to find certain ingredients or food items. The container scheduler 925 can also regulate the operating conditions of the containers for example, temperature, moisture content, ventilation, or time left until the container should be emptied (e.g., the food has expired). In some implementations, the container scheduler 925 can determine some containers are running low on ingredients or food items (e.g., below a weigh threshold) and communicate this information to the FSCU 905 to cause the system to automatically order more food from a third party or request the user order more food. The container scheduler 925 instructs the robotic arms 310 when and where to find ingredients or food items in containers. For example, the container scheduler 925 keeps address and bin location status and activity for the four station configurations for this system. If a void or a need to fill a container is detected (e.g., container is empty), the container scheduler 925 instructs the robotic arm 310 to resolve the problem and refill the container.

The antenna array controller 930 controls the antennas in the food system 105. The antenna array controller 930 can transmit and receive signals from antennas for all containers in the food system 105. The antenna array controller 930 can also adjust the frequency and power transmitted from antennas in the containers 305. The antenna array controller 930 can receive information form detectors associated with antennas transmitting RF waves inside of a container to determine refracted, reflected, or absorbed waves based on the food item. The antenna array 930 can implement radar algorithms, object recognition algorithms, or other detecting and analyze algorithms to identify a food item or portions of the food item. The antenna array controller 930 can also adjust the resolution of the antenna array by modifying the number of active antennas and detectors or properties of the RF waves used by the antennas.

The inventory analyzer 935 tracks inventory usage, housekeeping, maintenance, and operational costs (e.g., taxes, receipts, payments, stored cash). The inventory analyzer 935 can communication with third-party grocery services to order information or determine what is available for ordering.

The user analyzer 940 receives, processes, and analyzes user data. The user analyzer 940 can receive data from a user via an application (e.g., mobile app), the graphical user interface 110 (FIG. 1), or a third-party database (e.g., a user's profile, medical record, survey). The user analyzer 940 stores a user's preferred shopping list or history of a user's shopping lists. The user analyzer 940 can also include lists available at stores (e.g., Amazon) to inform a user about a recommended shopping list. The user analyzer 940 can ask a user to perform a customer survey or send healthy food tips to user in conjunction with using the food system 105 to implement those healthy food tips. The recipe implementer 945 can determine recipes for a user (e.g., by receiving a request, downloading one, or using a recipe algorithm to pick one).

The meal suggestion engine 950 makes meal suggestions for a user. The meal suggestion engine 950 can extract, display, and store in cumulative nutrition facts, and provide a warning message when the user takes more nutrition facts than their needs, and provide a suggestion to help the user select a meal. Also, the meal suggestion engine 950 can send the user's nutrition information to the grocery store when a user buys the food. The meal suggestion engine 950 can count the energy consumed by the user, and give the user a hint on how to adjust his or her nutrition/diet control. The meal suggestion engine 950 can use the United States Department of Agricultures (USDA) National Nutrient Database (NND) for nutrient information of 8789 foods as of Standard Reference Release 28. The meal suggestion engine 950 operates by examining each nutrient in turn. For each nutrient the prototype selects a random food from a list of foods that contain the highest amount of that nutrient.

These software modules can also communicate with: user health and diet database 955, shopping list database 960, third party shopper database 965, and decision database 970. The user health and diet database 955 stores information about the user including: contact information, height, weight, food allergies, medical conditions (e.g., diabetes), and other information to calculate a user's diet. For example, the user health and diet database 955 can store workout information and medical information and use this information to determine a recommended caloric intake for a user. The shopping list database 960 stores a user's preferred shopping list or history of a user's shopping lists. The shopping list database 960 can also include lists available at stores (e.g., Amazon) to inform a user about a recommended shopping list. The third-party shopper database 965 includes information about food available on third party websites (e g, Amazon Fresh, supermarket website). And the decision database 970 can access big data sets to learn about user behavior or to run machine learning algorithms (e.g., convolutional neural networks to determine what a user would like to eat based on his or her previous meals).

The CPU 955 can be a single processing unit or multiple processing units in a device or distributed across multiple devices. The CPU 955 can be coupled to other hardware devices, for example, with the use of a bus, such as a Peripheral Component Interconnect (PCI) bus or Small Computer System Interface (SCSI) bus. The CPU 955 can communicate with a hardware controller for devices, such as the graphical user interface 110 (FIG. 1). In some examples, the graphical user interface 110 provides graphical and textual visual feedback to a user. The CPU 955 can include an integration circuit (IC), an application specific IC (ASIC), or a field-programmable gate-array (FPGA).

The memory 910 can include one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, magnetic storage devices, tape drives, device buffers, and so forth. A memory is not a propagating signal divorced from underlying hardware; rather a memory is non-transitory. The memory 910 can include program memory that stores programs and software, such as an operating system and other application programs. The memory 910 can also include data memory that can include user data such as passwords, usernames, input text, audio, video, user preferences, and selections. Data memory can also include configuration data, settings, user options, time stamps, or session identifiers. Data in memory can be provided to the program memory or any element of the food system 105.

Although not shown in FIG. 9, the FSCU 905 can include a communication device capable of communicating wirelessly or wire-based with a network node. The communication device can communicate with another device or a server through a network using, for example, TCP/IP protocols.

The FSCU 905 can utilize the communication device to distribute operations across multiple network devices.

Figure 10:
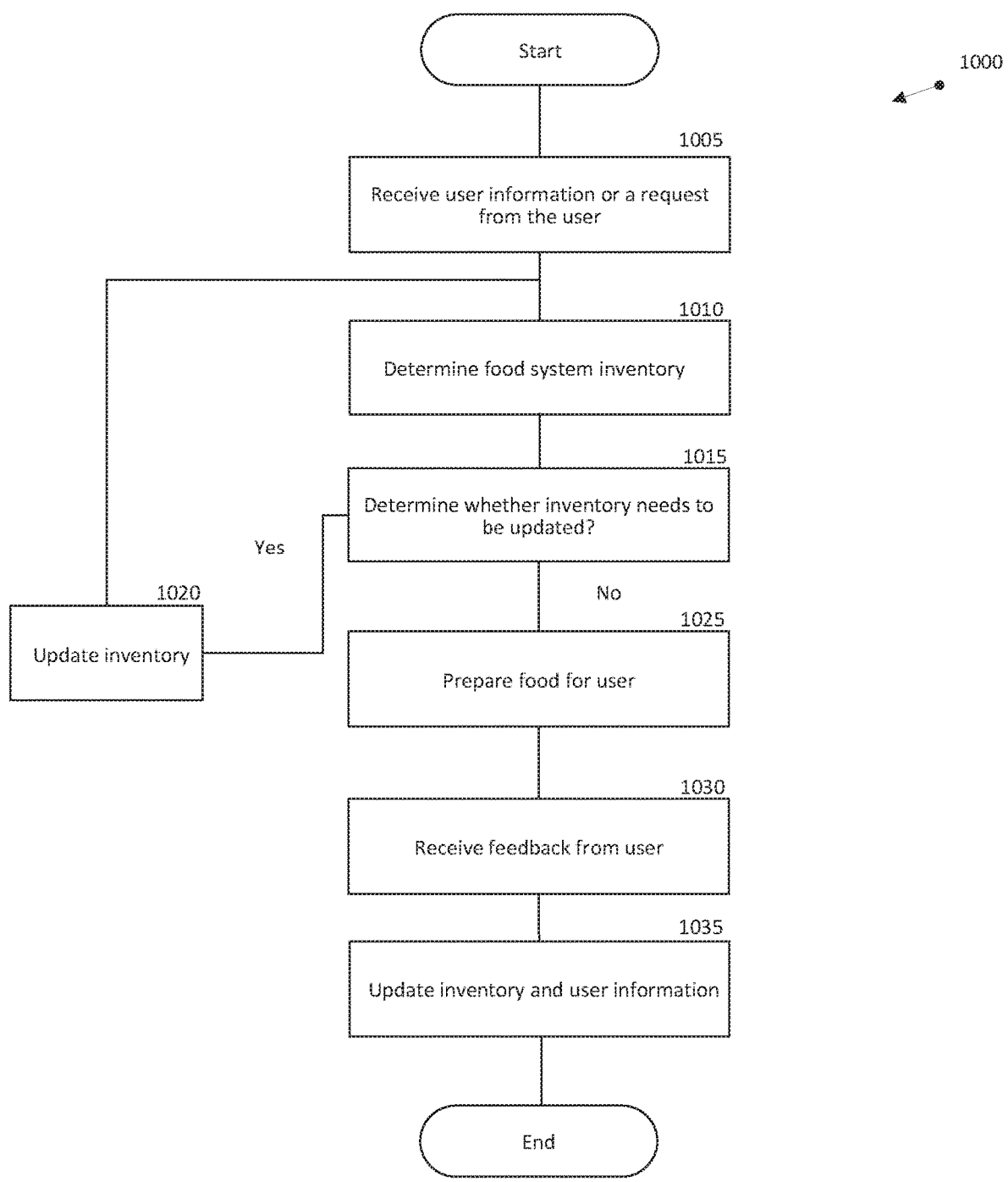
FIG. 10 is a flow diagram illustrating a process for preparing food in accordance with the disclosed technology.
Figure 11:
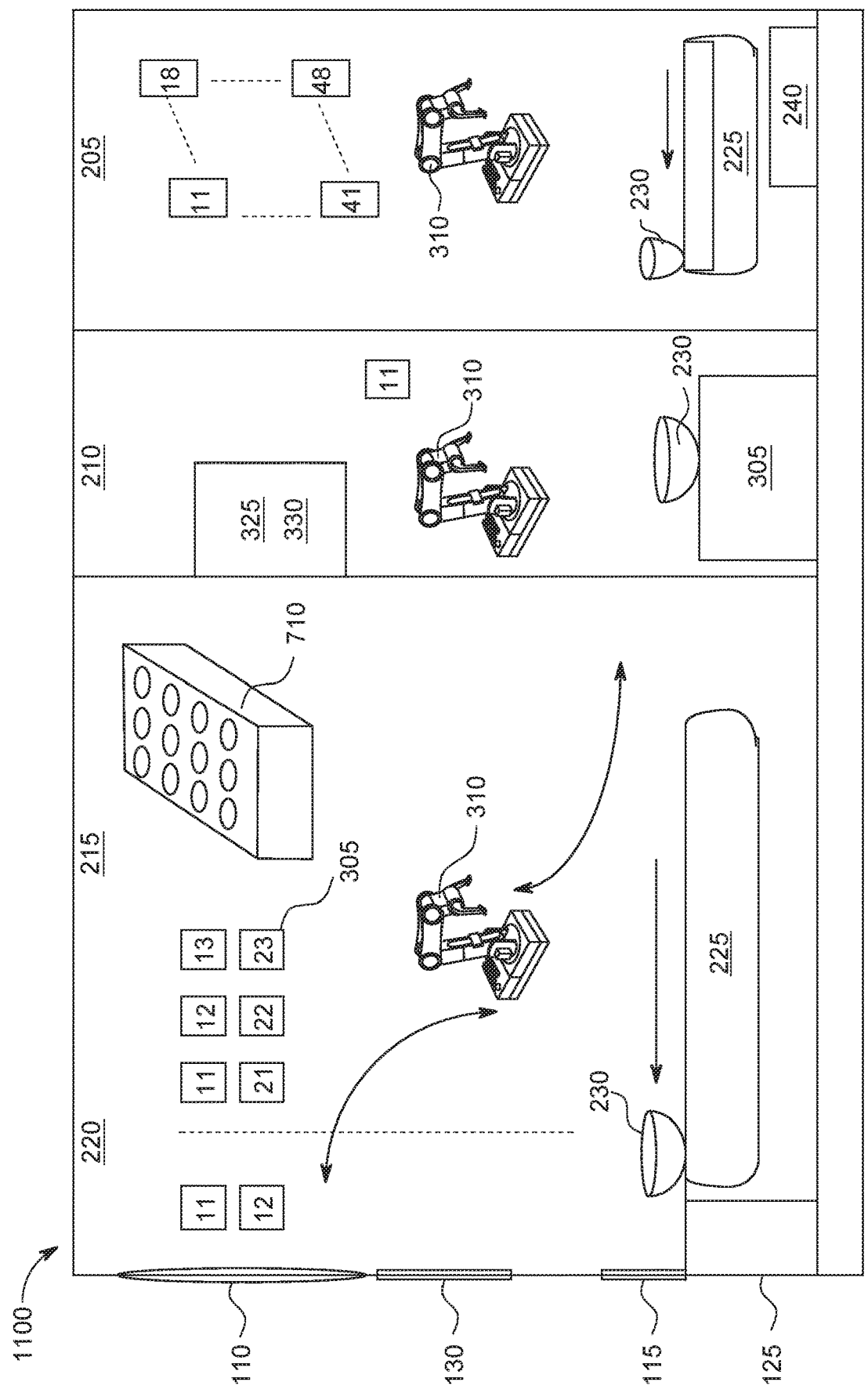
FIG. 11 is a flow diagram illustrating a process for modifying a food item for meal preparation in accordance with the disclosed technology.

FIG. 10 is a flow diagram illustrating a process preparing food in accordance with the disclosed technology. The process 1000 can be executed by the food system 105. The process 1000 can be begin when a user sets up the food system 105 in a home or business or when a user requests to have a meal prepare (e.g., salad).

At operation 1005, the food system receives user information or a request from the user. If the user grants permission, the food system 105 can gather person information about the user (e.g., exercise habits, weight, height, age, health, and other attributes) to determine the type of food and amount of food the user should eat to stay health. The user can input information related to health goals such as losing weight or avoiding certain unhealthy foods (e.g., high in fat or high in sugar). In some implementations, the user simple requests a specific meal (e.g., chicken salad) by inputting information on a graphical user interface of the food system. Once a user has input information, the food system 105 can remember the user with a user profile. In some implementations, the user profile is determined by a user inputting information from a health or diet app on a mobile device into the food system through an application program interface (API).

At operating 1010, the food system determines the food system inventory status. The food system can determine whether the system has the correct ingredients or food to prepare a recipe. The food system can determine the inventory status of containers in the food system 105. For example, the food system can use an antenna array inside the food system to determine the type of food in the system, the amount of food, the condition (e.g., good, bad, expired). Also, in this is operation, the food system 105 can dispose of food that expired or cut food that is partially expired of spoiled.

At decision operation 1015, the food system determines whether the inventory needs to be updated. Based on the operation 1010, the food system can determine that some food is expiring, has expired, or is not present. If the food system determines that it needs based user settings. For example, the food system 105 can determine that it should automatically order food or ingredients that are missing because the user granted permission for automatic refills.

At operating 1020, the food system updates the inventory. The food system can perform this operation by contacting the user to purchase food or ingredients. Alternatively, the food system can automatically order food or ingredients using the network (e.g., Amazon Fresh). In some implementations, this operation happens based on a user's preferences such as budget, preference for local food, dietary restrictions, or what is available in season and locally.

At operation 1025, the food system 105 prepares food for the user. As shown FIGS. 2-9, the food system can cook, cut, juice, and dispense a meal. In this operation, the food system can also dispose of food waste in the compost. At operation 1030, the food system receives feedback from user such as whether the user liked the meal or if the user finished the entire meal. At operation 1035, the food system updates inventory and user information for the food system. The process 1000 can be repeated or some operations can be repeated.

Figure 12:
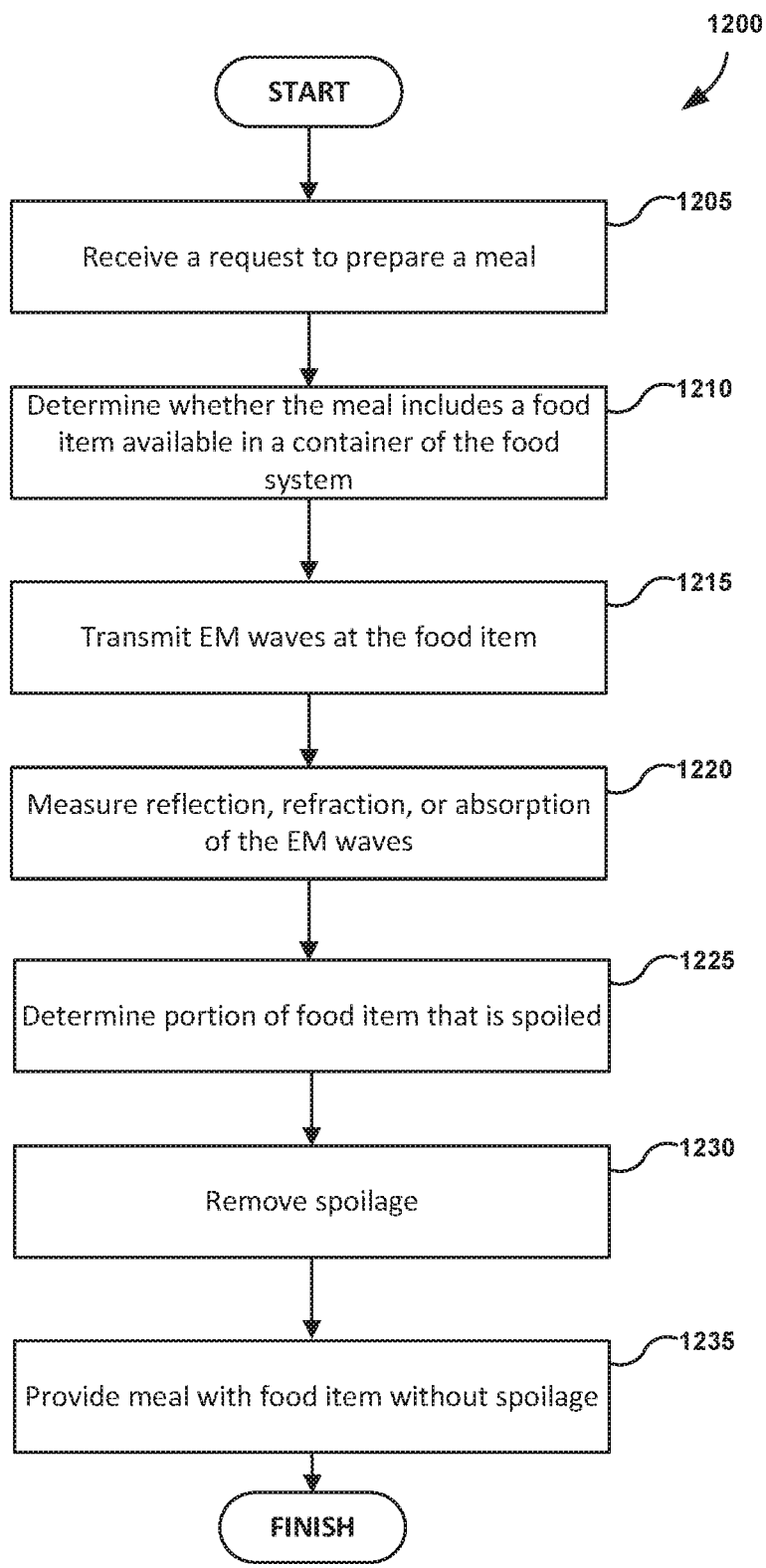
FIG. 12 is a schematic example of the food system configured to prepare salad in accordance with some implementations of the disclosed technology.

FIG. 12 is a flow diagram illustrating a process 1200 for modifying a food item for a meal. The food system 105 can execute the process 1200. The process 1200 can be begin after a user sets up the food system 105 in a home or business or when a user requests to have a meal prepared (e.g., salad).

At meal preparation operation 1205, the food system receives a request to prepare a meal. The user can request the meal using a mobile device (e.g., using a mobile application). The mobile device can transmit the request to the food system. Alternatively, the user can directly input his or her request into the food system using a graphical user interface (FIG. 2) or via a voice command. The user can also provide other information related to the meal such as food preferences (e.g., amount of dressing, temperature of meal, portion size). In some implementations, the food system can also receive diet or caloric information related to the user's diet (either directly from the user or from a server in communication with the food system).

At determining operation 1210, the food system determines whether the meal includes a food item available in a container of the food system. To determine if a food item is available, the food system can query its inventory (FIG. 9). The food system can also order the food item if the food system determines the food item is missing or is below a threshold level (e.g., the last apple). In some implementations, the food system receives a recipe and queries its inventory to determine which food items are required for that recipe.

At the transmit EM waves operation 1215, the food system transmits EM waves at the food item with an antenna array electronically coupled to the food system. The antenna array can be circular, linear, or other type of antenna array. The EM waves can be radio frequency or microwave frequency waves. To determine the type of EM waves to transmit, the food system can select a frequency that is safe or preferred for certain types of food. The frequency can be based on the dielectric properties of the food item or the dielectric properties of spoilage for the food item. For example, a food item that is spoiling has a higher concentration of enzymes that change the dielectric properties of the food item.

At measure operation 1220, the food system measures the reflection, refraction, or absorption of the EM waves. The food system can use a detection unit inside a container that includes the food item (FIG. 4B) to measure reflection, refraction, or absorption of the EM waves. The measurement of EM waves reflected, refracted, or absorption can be based on permittivity of the EM waves, measured reflection of the EM waves after hitting the food item, or other methods such as Radar. In some implementations, the food system uses two frequencies of EM waves: one to frequency that can penetrate the food item and another that can is reflected or absorbed.

At determine spoilage operation 1225, the food system determines that a location of the spoilage of the food item or determines the entire food item is soiled based on the measured reflection, refraction, or absorption of the EM waves. In some implementations, the food system determines that a food item is spoiled partially or completely based on approximately dielectric properties of the food item. The food system can also determine a location of spoilage based on water content or density of the food item location based on the measured EM waves. The food system can also use temperature information or storage item to further determine spoilage portions of the food item. In some implementations, the food system queries a database that includes previously tested values for food items that are not spoiled and compares these values to current values to determine if the food item of a portion of the food item is spoiled.

At remove spoilage operation 1230, the food system removes the spoilage. The food system can remove the spoiled area with a robotic arm (e.g., rotating blade, knife, blade, or cutting mechanism), a string (e.g., with tension), or a water jet. The food system can use the measurement information from measure operation 1220 to provide location coordinates for the spoilage. Based on the location coordinates, the robotic arm, the string, or the water jet can remove the spoilage. If it is determined that the entire food item is spoiled, the food system can dispose of the entire food item using the disposal system. At provide meal operation 1235, the food system provides the meal with the food item with removed spoilage.

The process 1200 can be repeated entirely or partially. For example, the food system can prepare another food item that is necessary for a meal. The process 1200 can be stored in a computer-readable medium and executed by a processor of the food system; accordingly, the process 1200 can be computer-implemented methods.

CONCLUSION

Reference in this specification to "one implementation" or "an implementation" means that a feature, structure, or characteristic described about the implementation is included in at least one implementation of the disclosure. The appearances of the phrase "in one implementation" in various places in the specification are not necessarily all referring to the same implementation, nor are separate or alternative implementations mutually exclusive of other implementations. Moreover, various features are described that can be exhibited by some implementations and not by others. Similarly, various requirements are described which may be requirements for some implementations but no other implementations.

The techniques introduced here can be embodied as special-purpose hardware (e.g., circuitry), as programmable circuitry appropriately programmed with software and/or firmware, or as a combination of special-purpose and programmable circuitry. Hence, implementations may include a machine-readable medium having stored thereon instructions which may be used to program a computing device (e.g., the food system) to perform a process. The machine-readable medium may include, but is not limited to, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Machine-readable mediums can include tangible non-transitory computer-readable mediums excluding transitory signals.

The following description and drawings are illustrative and are not to be construed as limiting. Numerous specific details are described to provide a thorough understanding of the disclosure. However, in certain instances, well-known or conventional details are not described in to avoid obscuring the description. References to one or an implementation in the present disclosure can be, but not necessarily are, references to the same implementation; and, such references mean at least one of the implementations.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, if it is highlighted. It will be appreciated that same thing can be said in more than one way.

Consequently, alternative language and synonyms may be used for any one or more of the terms discussed herein, nor is any special significance to be placed upon if a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various implementations given in this specification.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

What is claimed is:

1. A system to prepare a meal, the system comprising:
   a robotic arm configured to move, rotate, or modify a food item;
   an antenna array configured to transmit electromagnetic (EM) waves at the food item;
   a detection unit to measure reflection, absorption, or refraction of the EM waves by the food item;
   a container configured to store the food item;
   a water jet, knife, or string to cut the food item; and
   a processor coupled to a memory, the memory storing instructions that when executed by the processor cause the system to:
   receive a request for preparing a meal including the food item;
   determine whether the food item has spoilage based on the measurement of refraction, reflection, or absorption of the EM waves;
   remove spoilage from the food item by cutting the food item with the water jet, the knife, or the string; and
   provide the meal with the food item,
      wherein the spoilage is removed from the provided food item in the meal.

2. The system of claim 1, the system further comprises:
   a camera, and
   wherein the instructions further include identifying the food item based on an image captured by the camera.

3. The system of claim 1, the system further comprises:
   an ultra violet (UV) light configured to shine UV light on the food item.

4. The system of claim 1, the system further comprising:
   a graphical user interface to receive a request from a user;
   a temperature sensor configured to detect a temperate of the food item or the container storing the food item,
      wherein determining whether the food item has spoilage is partially based on a temperature measurement from the temperature sensor.

5. The system of claim 1, the system further comprising:
a composting unit to compost food waste,
   wherein the food waste is associated with the spoilage of the food item.

6. The system of claim 1, the system further comprising:
an ingredient dispensing unit configured to dispense ingredients,
   wherein the ingredient dispensing unit includes a rotational ingredient belt.

7. The system of claim 1, wherein the system is configured to fit inside of a kitchen and is portable.

8. The system of claim 1, the system further comprising:
an inventory analyzer configured to communicate with a grocery delivery service.

9. The system of claim 1, wherein the antenna array is a linear array, circular array, and planar array.

10. A method to prepare a meal, the method comprising:
receiving, at the food system, a request to prepare a meal;
determining, at the food system, that the meal includes a food item available in a container of the food system;
transmitting, by an antenna array electronically coupled to the food system, electromagnetic (EM) waves at the food item;
measuring the reflection, refraction, or absorption of the EM waves;
determining that the food item has a portion of spoilage and determining a location of the spoilage of the food item based on the measured reflection, refraction, or absorption of the EM waves;
removing, with a robotic arm of the food system, part of the spoilage for the food item; and
providing the food item with removed spoilage as the meal.

11. The method of claim 10, the method further comprising:
weighing food items stored in the food system; and
adjusting a size of the food item based on a recommended caloric intake for a user.

12. The method of claim 10, the method further comprising:
determining a food system lacks the ingredients to prepare the meal;
sending a notification to a server to provide the missing ingredient in response to determine the system lacks the ingredient; and
receiving the missing ingredient.

13. The method of claim 10, the method further comprising:
washing the food item with an internal water system; or
washing a container with the internal water system.

14. The method of claim 10, the method further comprising:
disposing of the spoilage in compost.

15. The method of claim 10, wherein the EM waves are microwave frequency waves, or radio frequency waves.

16. A non-transitory computer-readable medium storing instructions that when executed by a processor cause a device to perform operations to prepare food, the operations comprising:
receiving, at the food system, a request to prepare a meal;
determining, at the food system, that the meal includes a food item available in a container of the food system;
transmitting, by an antenna array electronically coupled to the food system, electromagnetic (EM) waves at the food item;
measuring the reflection, refraction, or absorption of the EM waves;
determining that the food item has a portion of spoilage and determining a location of the spoilage of the food item based on the measured reflection, refraction, or absorption of the EM waves;
removing, with a robotic arm of the food system, part of the spoilage for the food item; and
providing the food item with removed spoilage as a meal.

17. The non-transitory computer-readable medium of claim 16, wherein measuring the reflection, refraction, or absorption of the EM waves includes querying a database to determine the dielectric properties associated with the food item or spoilage for the food item.

18. The non-transitory computer-readable medium of claim 16, wherein the EM waves are microwave frequency waves or radio frequency waves.

19. The non-transitory computer-readable medium of claim 16, the instructions further comprising:
periodically scanning containers in the food system to determine an inventory of food items;
providing a user with a list of available food items or available meals based on the periodically scanned items.

20. The non-transitory computer-readable medium of claim 16, the instructions further comprising:
washing the food item with an internal water system;
communicating, with a meal suggestion engine, to determine an advised meal or meal portion for a user; and
disposing of the spoilage in compost.

* * * * *